(12) United States Patent
Lerchen et al.

(10) Patent No.: US 7,132,295 B2
(45) Date of Patent: Nov. 7, 2006

(54) ISOTOPICALLY CODED AFFINITY MARKERS 3

(75) Inventors: Hans-Georg Lerchen, Leverkusen (DE); Hans-Ulrich Siegmund, Leverkusen (DE); Dorian Immler, Leverkusen (DE); Andreas Schumacher, Erfringen-Kirchen (DE); Daniel Auriel, Leichlingen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 18 days.

(21) Appl. No.: 10/494,999

(22) PCT Filed: Oct. 30, 2002

(86) PCT No.: PCT/EP02/12105

§ 371 (c)(1),
(2), (4) Date: Oct. 29, 2004

(87) PCT Pub. No.: WO03/040288

PCT Pub. Date: May 15, 2003

(65) Prior Publication Data

US 2005/0049406 A1    Mar. 3, 2005

(30) Foreign Application Priority Data

Nov. 9, 2001   (DE) ................. 101 54 745
Jul. 29, 2002   (DE) ................. 102 34 415

(51) Int. Cl.
| G01N 24/00 | (2006.01) |
| G01N 33/532 | (2006.01) |
| C07C 335/16 | (2006.01) |
| C07D 291/06 | (2006.01) |
| A61K 51/04 | (2006.01) |

(52) U.S. Cl. .......... 436/173; 436/531; 436/544; 435/7.5; 544/1; 564/26; 562/575; 424/1.65

(58) Field of Classification Search ............ 544/1; 436/531, 173, 544; 424/1.65; 435/7.5; 564/26; 562/575
See application file for complete search history.

(56) References Cited

U.S. PATENT DOCUMENTS 4,190,647 A * 2/1980 Goldstein et al. ............ 514/17

FOREIGN PATENT DOCUMENTS

WO    F1 0011208    2/2000

* cited by examiner

*Primary Examiner*—Long V. Le
*Assistant Examiner*—Shafiqul Haq

(57) ABSTRACT

This application relates to isotopically labeled affinity markers of the formula (II)

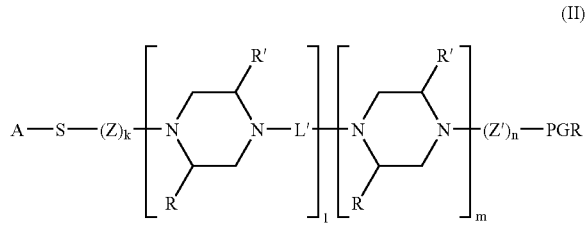

Figure 1:
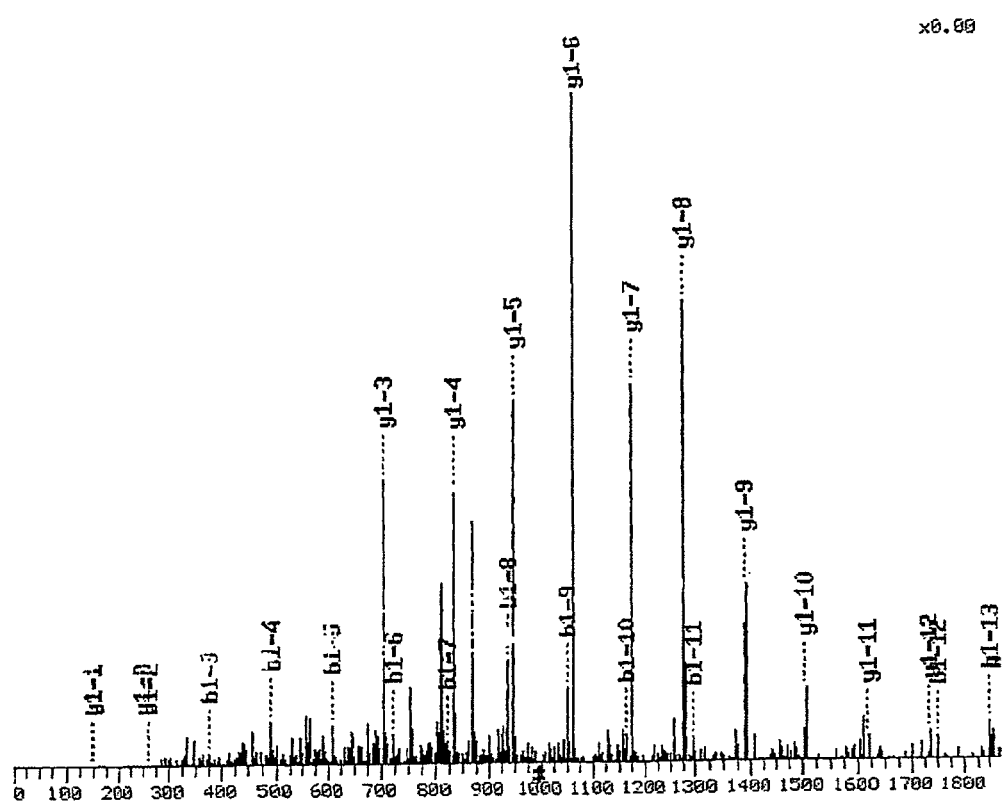

for mass spectrometric analysis of proteins. In formula (II), the groups A, PRG, S, Z, L', Z', R, R', k, l, m, and n are as defined in the claims. The application also provides a process for preparing these materials, a method for analyzing proteins using such materials, and a kit containing one or more of these materials.

10 Claims, 4 Drawing Sheets

ISOTOPICALLY CODED AFFINITY MARKERS 3

The invention relates to novel, isotope-coded affinity tags for the mass-spectrometric analysis of proteins, and to their preparation and use.

Proteomics technology opens up the possibility of identifying novel biological targets and tags by means of analyzing biological systems at the protein level. It is known that only a certain proportion of all the possible proteins encoded in the genome is being expressed at any given time, with, for example, tissue type, state of development, activation of receptors or cellular interactions influencing the pattern and rates of expression. In order to detect differences in the expression of proteins in healthy or diseased tissue, it is possible to make use of a variety of comparative methods for analyzing protein expression patterns ((a) S. P. Gygi et al., Proc. Natl. Acad. Sci. U.S.A., 2000, 97, 9390; (b) D. R. Goodlett et al., Proteome Protein Anal. 2000, 3; (c) S. P. Gygi et al., Curr. Opin. Biotechnol., 2000, 11, 396).

The mass-spectrometric detection of proteins is a powerful method in this connection. When affinity tags which have been isotope-coded differentially (ICAT®=isotope coded affinity tags) and tandem mass spectrometry are used, this method can be enlisted for quantitatively analyzing complex protein mixtures ((a) S. P. Gygi et al., Nature Biotechnology, 1999, 17, 994; (b) R. H. Aebersold et al., WO 00/11208). The method is based on each of two or more protein mixtures, which are to be compared and which have been obtained in different cell states, being reacted with an affinity tag of a different isotope coding. After that, the protein mixes are combined, where appropriate fractionated or treated proteolytically and purified by affinity chromatography. After the bound fragments have been eluted, the eluates are analyzed by a combination of liquid chromatography and mass spectrometry (LC-MS). Pairs or groups of peptides which are labeled with affinity tags which only differ in the isotope coding are chemically identical and are eluted virtually simultaneously in the HPLC; however, they differ in the mass spectrometer by the respective molecular weight differences due to the affinity labels having different isotope patterns. Relative protein concentrations can be obtained directly by carrying out measurements of the peak areas. Suitable affinity tags are conjugates composed of affinity ligands which are linked covalently to protein-reactive groups by way of bridge members. In connection with this, different isotopes are incorporated into the bridge members. The method was described using affinity tags in which hydrogen atoms were replaced with deuterium atoms ($^1H/^2D$ isotope coding).

The method using $^1H/^2D$ isotope-coded affinity tags which is described in the prior art suffers from a variety of disadvantages, in particular an isotope effect of the differently labeled, but otherwise identical, peptide fragments in the LC, inadequate stability of the affinity tags in general and especially in LC-MS/MS, a lack of efficiency as regards the avidin monomer-based affinity chromatography, and a lack of flexibility in regard to the incorporation of the isotope labels.

The object of the present invention was to make available improved isotope-coded affinity tags.

The invention relates to organic compounds which are suitable for use as affinity tags for the mass-spectrometric analysis of proteins, of the formula (I), $$A-L-PRG \qquad (I)$$

in which
A is an affinity ligand residue or a solid phase,
PRG is a protein-reactive group, and
L is a linker which covalently links A and PRG,
where the linker L contains a group of the formula (I')

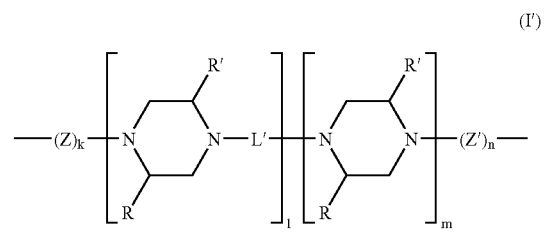

in which
Z is the amino acid residue NH—$CHR^x$—$(CH_2)_x$—CO, with the amino acid side chain being $R^x$ and the number x being selected from the range of 0 to 5,
L' is a bridge which makes possible or facilitates a covalent linkage of two piperazine residues or, in the case of $l \geq 2$, are identical or different bridges of this nature,
R and R' are in each case an α-amino acid side chain on a piperazine ring, which side chains are independent of each other and independent of other R and R' on other piperazine rings belonging to the same running variable or the other of the two running variables 1 and m,
Z' is the amino acid residue CO—$(CH_2)_y$—$CHR^y$—NH, with the amino acid side chain being $R^y$ and the number y being selected from the range of 0 to 5, with Z' differing from Z in the different orientation in regard to the terminal CO and NH groups, and
k, l, m and n are, independently of each other, in each case a number from 0 to 10, with the sum k+l+m+n being at least 1 and at most 40, or the salts thereof.

As compared with the prior art, the affinity tags in accordance with the invention exhibit the following advantages, in particular:

deuterium, $^{13}C$-labelled or $^{13}C$-labelled and $^{15}N$-labelled glycine building blocks, or other correspondingly labeled amino acid building blocks, are inexpensive starting materials which make it possible to construct the isotope-labeled affinity tags in a flexible manner. More than twenty $^{13}C$ labels and, in addition, up to ten $^{15}N$ isotopes can be readily introduced into the affinity tag which is described in the formula (I). In contrast to the previously described affinity tags having a markedly smaller mass difference (ΔM=8), it is also possible, in this way, to analyze in parallel several proteome samples by respectively modifying with affinity tags having various mass differences. Preference is given to the embodiment using up to 4 differently labeled affinity tags, which permit the simultaneous analysis and relative quantification of up to 4 complex proteome samples.

The modular construction of the affinity tags permits a flexible combination of the individual building blocks, which combination matches the requirements of the operational program.

The affinity tags which are described can be equipped with an acid-labile predetermined breaking point which enables the peptide fragments to be decomplexed by means of a substantially more efficient affinity chromatography, which is based, for example, on streptavidin or oligomeric avidin in the case of the biotin-modified peptide fragments, or by means of reversible binding to a solid phase. Furthermore, the tags which remain on the peptide fragments following acid cleavage have a low molecular weight and a high isotope density.

The manipulation of the affinity tags is improved as the result of an improvement in solubility, as the result of being in a crystalline or amorphous state and as the result of an increase in stability.

The invention furthermore relates to the use of one or more compounds according to the invention, which are isotope-labeled differently, as reagents for the mass-spectrometric analysis of proteins, in particular for identifying one or more proteins or protein functions in one or more protein-containing samples, and for determining the relative expression levels of one or more proteins in one or more protein-containing samples.

enter into noncovalent interactions with fixed lectins, for example, as affinity ligands. It is furthermore possible to use the interaction of haptens with antibodies, or the interaction of transition metals with corresponding ligands, as complexing agents, or other systems which interact with each other, in the same sense.

Alternatively, the selective enrichment can also be achieved by means of selective, reversible binding to an appropriately functionalized solid phase A. Examples of suitable solid phases are amino-functionalized resins based on silica gel and, furthermore, those known from the peptide syntheses carried out as solid phase syntheses, such as trityl resin, Sasrin resin, which is based on benzyl alcohol supportation, Wang resin, which is based on benzyl alcohol supportation, Wang polystyrene resin, Rink amide MBHA resin or TCP (trityl chloride polystyrene) resin (in the formulae which are depicted, the encircled P in each case represents the resin residue):

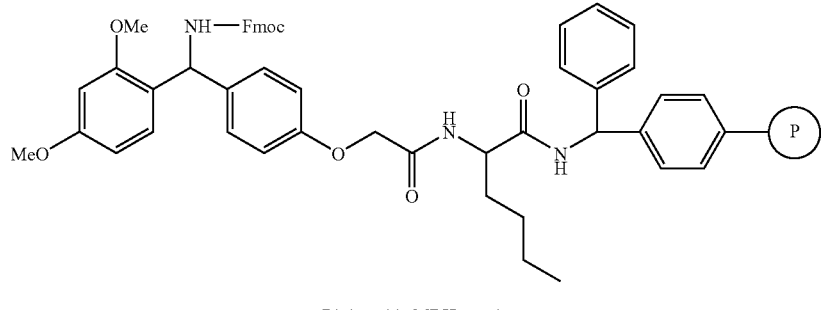

Rink amide MBHA resin

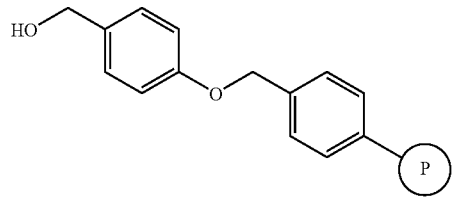

Wang resin

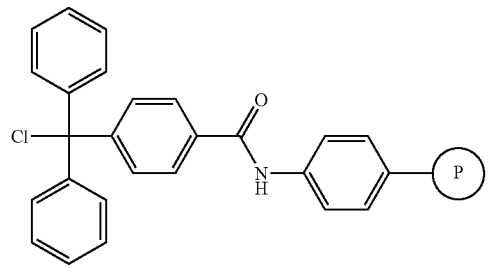

TCP resin

The invention furthermore relates to a kit for the mass-spectrometric analysis of proteins, which kit contains, as reagents, one or more compounds according to the invention which are isotope-labeled differently.

An affinity ligand A is used for selectively enriching samples by means of affinity chromatography. The affinity columns are provided with the corresponding reactants which are complementary to the affinity ligands, and which enter into covalent or noncovalent bonds with the affinity ligands. An example of a suitable affinity ligand is biotin or a biotin derivative, which enters into strong, noncovalent bonds with the complementary peptides avidin or spectravidin. In this way, it is possible to use affinity chromatography to selectively isolate samples to be investigated from sample mixtures. In the same sense, it is also possible for example, to use carbohydrate residues, which are able to A polymeric support, in particular a modified natural or synthetic resin, for example a resin based on silica gel or polyethylene glycol, which possesses functional groups, such as hydroxyl, carboxyl and amino groups, in particular amino groups, which are suitable for binding on the linker L, is preferred as the solid phase A. An amino-functionalized resin based on silica gel, for example an aminopropyl silica gel as is marketed, for example, by Aldrich under the number 36425-8, is particularly preferred as the solid phase A.

Protein-reactive groups, PRG, are used for selectively labeling the proteins at selected functional groups. PRGs have a specific reactivity for terminal functional groups in proteins. Examples of amino acids which, as elements or proteins, are frequently used for selective labeling, are mercaptoaminomonocarboxylic acids, such as cysteine, diaminomonocarboxylic acids, such as lysine or arginine, or monoaminodicarboxylic acids, such as aspartic acid or glutamic acid. Furthermore, protein-reactive groups can also be phosphate-reactive groups, such as metal chelates, and also aldehyde-reactive and ketone-reactive groups, such as semicarbazones or else amines, accompanied by subsequent treatment with sodium borohydride or sodium cyanoborohydride. Protein-reactive groups can also be groups which, following a selective protein derivatization, such as a cyanogen bromide cleavage, or an elimination of phosphate groups, etc., react with the reaction products.

Z and Z' are residues of identical or different amino acids. Preference is given to residues of L-α-amino acids, in particular the 20 natural proteinogenic amino acids (x=0 or y=0), for example glycine residues, and residues of ω-amino acids, such as NH—$(CH_2)_2$—CO and CO—$(CH_2)_2$—NH. In this connection, the amino acids can, where appropriate, be in the D, L or racemic form.

Preferred compounds according to the invention of the formula (I) possess, in the linker L, as the group of the formula (I'), a group of the formula (I'') (all the R and R' in formula (I') are hydrogens):

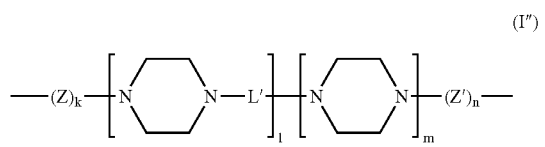

Compounds according to the invention of the formula (I) which are likewise preferred possess, in the linker L, a group of the formula (I'), in particular a group of the formula (I''), in which Z is the glycine residue NH—$CH_2$—CO or Z' is the glycine residue CO—$CH_2$—NH, in particular in which Z is the glycine residue NH—$CH_2$—CO and Z' is the glycine residue CO—$CH_2$—NH.

In another embodiment, preference is given to linkers L which possess a predetermined breaking point S, such as an acid-labile functionality, which, under particular conditions, for example under the influence of acid, guarantee cleavage of the affinity tag in order, in this way, for example, to facilitate release from the affinity column or to reduce the size of the residue remaining on the peptide or to make the operational procedures as a whole more efficient. Instead of using an acid-labile predetermined breaking point, it is also possible to bring about the cleavage of the linkers L in another manner, for example by chemical cleavage of, inter alia, silyl ethers, esters, carbamates, thioesters, acetals, disulfides or Schiff's bases, and, furthermore, by means of photochemical cleavage or by means of the enzymic cleavage of esters, amides, nucleotides or glycosides or by means of thermal cleavage, for example of interacting nucleic acid strands.

In order to improve the solubility of the affinity tags according to the invention, it is possible to prepare and employ acid and/or basic functional groups which are present in the form of their salts, preferably their hydrochlorides, acetates, trifluoroacetates, alkali metal salts or ammonium salts.

In one particular embodiment of the invention, the protein-reactive group PRG possesses solubility-improving functional groups.

Preferred compounds according to the invention are those of the formula (I), in particular of the formula (II),

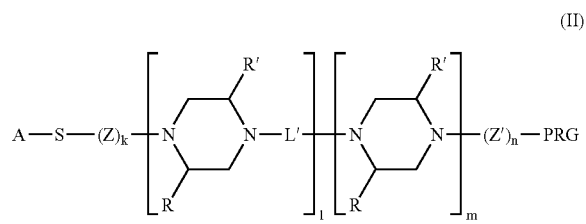

in which one or more of the groups A, PRG, S, Z, L', Z' and k, l, m and n, in particular all these groups, are selected in accordance with the following definitions:

A is the acyl residue of an affinity ligand, for example biotinyl or a biotin derivative, or is a functional group which is bound to a polymeric support, for example a support-bound hydroxyl, carboxyl or amino group, in particular a support-bound amino group.

PRG is the residue of a protein-reactive group which is characterized by an electrophilic group and a suitable bridge which makes possible, and facilitates, the bonding of the electrophilic group to Z'. furthermore, such a group can, by means of being configured appropriately, also improve the solubility, for example. A preferred protein-reactive group is an epoxide, a maleimido group, a halogen or an acrylic residue, in particular bridged electrophiles such as

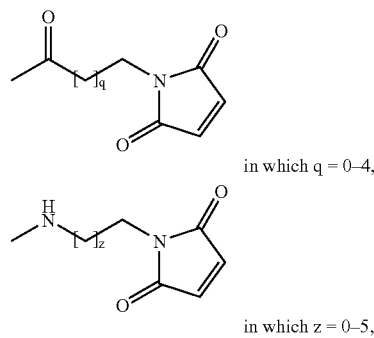

in which q = 0–4, in which z = 0–5,

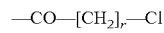

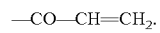

in which r=1–10,

Furthermore, PRG can be another known protein-reactive group, as were described and summarized, for example, by W. H. Scouten in Methods in Enzymology, Volume 135, edited by Klaus Mosbach, AcademicPress Inc. 1987, pp. 30 ff.

S is an acid-labile predetermined breaking point, such as

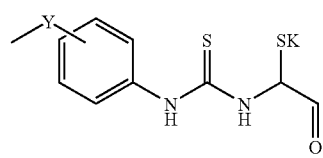

in which Y is a spacer, preferably having 1–10, in particular 1–5, non-hydrogen atoms, which makes possible or facilitates, the binding of the aryl residue to the affinity ligands or to the polymeric support, particularly preferably NH, NH—CH$_2$, NH—CH$_2$—CH$_2$—NH—CO or CH$_2$—CO, where Y can be in the ortho, meta or para position in relation to NH and the para position is preferred, and in which SK is the side chain residue of an α-amino acid of the formula SK—CH(NH$_2$)—COOH, which, in the case of SKs other than an H atom, can be present in the D, L or racemic form, for example the side chains of the 20 natural amino acids and their D forms and racemates.

Z is the residue of an amino acid, in particular the residue of glycine which is not labeled or which can contain $^{13}$C or $^{15}$N labels, or a combination of these labels.

L' is a bridge which makes possible, or facilitates, the covalent linkage of two piperazine residues. L' is preferably composed of the building blocks alkylene, in particular (CH$_2$)$_s$, alkenylene, alkynylene, arylene, CO, CS and NH, in particular composed of a number of from 2 to 10 of these building blocks. L' can contain other amino acid residues, such as Z and Z', in particular glycine residues, which can, where appropriate, contain $^{13}$C or $^{15}$N isotope labels or a combination of these labels, and is preferably a bridge selected from CO—CO, CO—(CH$_2$)$_s$—CO and also CO-arylene-CO, CO—CH$_2$—NH—CO—NH—CH$_2$—CO, CO—NH—CH$_2$—CO, CO—CH$_2$—NH—CO, CO—CH$_2$—NH—CO—CO—NH—CH$_2$—CO, CO—CH$_2$—NH—CO—(CH$_2$)$_s$—CO—NH—CH$_2$—CO, CO—CH$_2$—NH—CO—arylene-CO—NH—CH$_2$—CO, (CH$_2$)$_s$—NH—CO—CO—NH—(CH$_2$)$_s$, (CH$_2$)$_3$—NH—CO—CO—NH—(CH$_2$)$_3$, (CH$_2$)$_s$—CO, (CH$_2$)$_2$—CO, CO and CS, where s is preferably an integer between 1 and 6, for example 2, 3, 4 or 5.

R and R' on a piperazine ring are in each case identical amino acid side chains, in particular hydrogen, and are preferably identical amino acid side chains, in particular hydrogen, on all the piperazine rings belonging to one of the two running variables l and m, and are particularly preferably identical amino acid side chains, in particular hydrogen, on all the piperazine rings.

Z' is the residue of an amino acid, in particular the residue of glycine, which differs from Z in the different orientation in regard to the terminal CO and NH groups; it may not be labeled or may contain $^{13}$C or $^{15}$N labels, or a combination of these labels.

k, l, m and n can, independently of each other, in each case be numbers between 0 and 10, where the sum of k+l+m+n is preferably greater than 0 and less than 20, and is particularly preferably less than 10. m is preferably the number 0 or 1.

Within the context of the present invention, alkyl, alkylene, alkenylene, alkynylene, alkoxy and arylene have the following meaning, unless otherwise specified:

Alkyl per se, and "alk" and "alkyl" in alkylene, alkenylene, alkynylene and alkoxy, are a linear or branched alkyl radical having as a rule from 1 to 6, preferably from 1 to 4, particularly preferably from 1 to 3, carbon atoms, by way of example and preferably methyl, ethyl, n-propyl, isopropyl, tert-butyl, n-pentyl and n-hexyl.

Alkylene, alkenylene and alkynylene are bivalent alkyl groups which, in the case of alkenylene or alkynylene, possess one, two, three, four, five or more double or triple bonds and correspondingly possess at least 2 carbon atoms, for example and preferably methylene, ethylene, ethenylene, ethynylene, n-propylene, isopropylene, n-propenylene, methylethenylene and propynylene.

Alkoxy is, by way of example and preferably, methoxy, ethoxy, n-propoxy, isopropoxy, tert-butoxy, n-pentoxy and n-hexoxy.

Arylene is a bivalent mono- to tricyclic aromatic carbocyclic radical having as a rule from 6 to 14 carbon atoms, by way of example and preferably phenylene, naphthylene and phenanthrenylene.

An amino acid tertiary function which may, where appropriate, be present in an amino acid side chain R, R', R$^x$, R$^y$, or SK can optionally be present in free form or protected with a protecting group. In one particular embodiment, the side chains, in particular SK, contribute to improving the solubility of the affinity tags.

The non-isotope-labeled compounds already constitute one isotope coding. For further isotope coding, the compounds according to the invention are preferably isotope-labeled with at least one carbon atom of the isotope $^{13}$C, in particular from four to 20 $^{13}$C atoms. The disadvantageous isotope effect which was observed in LC when using $^1$H/$^2$D isotope-coded affinity tags is markedly reduced, and even not evident at all, in the case of $^{12}$C/$^{13}$C isotope coding. Alternatively or in addition, it is also possible to use the isotopes $^2$D, $^{15}$N, $^{17}$O, $^{18}$O and/or $^{34}$S for the labeling.

In a particular embodiment of the invention, $^{13}$C-labeled compounds are additionally isotope-labeled with at least one nitrogen atom of the isotope $^{15}$N, preferably from one to ten $^{15}$N atoms, in particular from one to three $^{15}$N atoms.

The isotope labelings are generally carried out in L and/or PRG, preferably in L and, in that case, in particular in the groups Z, L' and Z' and/or in the piperazine building blocks.

The compounds according to the invention can, for example, be prepared by initially preparing an intermediate of the formula (III)

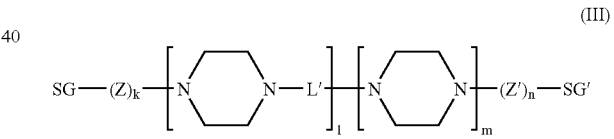

(III)

which is protected with suitable orthogonal protecting groups SG and SG', for example with the Boc group and the Fmoc group, in accordance with formula (III')

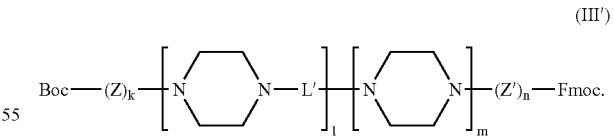

(III')

These intermediates are synthesized using classical methods of peptide chemistry as are known to a skilled person and as have been described, for example, in Houben-Weyl; Methoden der Organischen Chemie [Methods of organic chemistry]; fourth edition; volume XV parts 1 and 2; Georg Thieme Verlag Stuttgart 1974, or in Hans-Dieter Jakubke and Hans Jeschkeit: Aminosäuren, Peptide, Proteine [Amino acids, peptides, proteins]; Verlag Chemie, Weinheim 1982.

Standard reactions are first of all used to detach the protecting group SG once again from these intermediates and, after that, where appropriate, another amino acid derivative, which carries a protecting group SG which is identical to, or different from, the detached protecting group, in particular a Boc group, on the α-amino function, is attached, with derivatives of the formula (IV) being obtained. Tertiary functions which may be present in SK can optionally be present in protected form of in free form. Protecting groups which are optionally present can be retained permanently or be detached in separate unblocking steps or at the same time as the elimination of one of the terminal protecting groups.

A-NH$_2$, or an activated form thereof, is reacted, under suitable coupling conditions, with a compound

(VII)

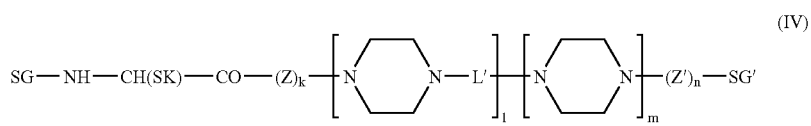

(IV)

Subsequently, piperidine in DMF can be used to detach the protecting group SG', for example an Fmoc group, from (IV) such that, in the next step, the coupling with the derivative of a protein-reactive group or the activated precursor of the derivative of a protein-reactive group of the formula

U-PRG (V)

in which U is a group which permits the linkage of PRG to Z' or, where appropriate, to another end group of L, by, for example, becoming a leaving group, can take place. Examples of such groups are, activated esters, such as N-hydroxysuccinimide esters, or chlorides or groups from which a leaving group can be generated during the coupling.

In a further step, the terminal protecting group SG is then detached, resulting in a conjugate of the formula (VI) being obtained.

which can optionally also carry a protecting group, to give the derivative

(VIII)

Activated carbonic acid derivatives, such as thiophosgene or thiocarbonyl-bisimidazole, are then used to convert the

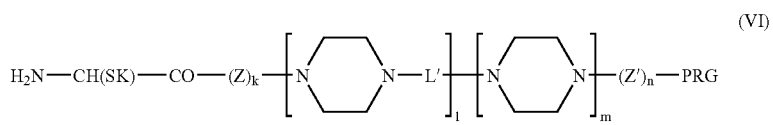

(VI)

In parallel with this, an affinity ligand A-OH or A-NH$_2$, or an activated form thereof, such as an activated ester, an acid chloride or the like, or a hydroxyl-functionalized, carboxyl-functionalized or amino-functionalized solid phase A-OH or derivative (VIII), where appropriate after prior elimination of an optionally introduced protecting group, into a corresponding isothiocyanate, which is then coupled to (VI) to give the thiourea (IX).

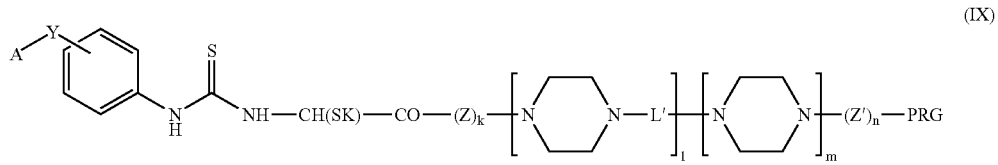

(IX)

For example, the amino function on resins can initially be reacted with Fmoc-protected p-aminobenzoic acid or with Fmoc-protected p-aminophenylacetic acid; subsequently, the Fmoc group can be detached and the compound converted into the isothiocyanate using an activated carbonic acid derivative; the isothiocyanate can then be converted into the thiourea.

The invention consequently also relates to a process for preparing a compound as claimed in claim 1, in which process i) a protected intermediate of the formula (III)

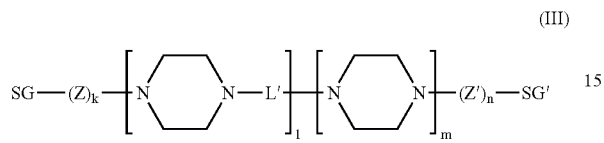

(III)

in which SG and SG' are two orthogonal protecting groups,
is prepared, ii) the protecting group SG is first of all detached from the intermediate of the formula (III) and, after that, another amino acid derivative, which carries a protecting group SG, which is identical to, or different from, the detached protecting group, on the α-aminofunction, is attached, with a derivative of the formula (IV),

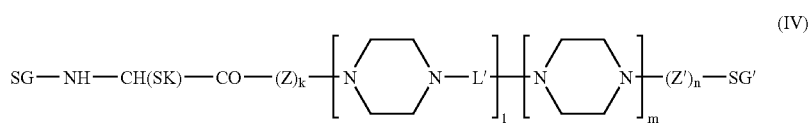

(IV)

in which SK is the side chain of an amino acid, being obtained, iii) after the protecting group SG' has been detached from the derivative of the formula (IV), the latter is reacted with the derivative of a protein-reactive group or the activated precursor of the derivative of a protein-reactive group of the formula (V)

U-PRG     (V)

in which U is a group which enables PRG to be linked to Z' or, where appropriate, to another end group of L, iv) the terminal protecting group SG is detached, with a conjugate of the formula (VI)

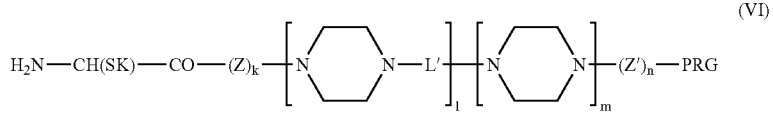

(VI)

being obtained, v) an affinity ligand A-OH or A-NH$_2$, or a hydroxyl-functionalized, carboxyl-functionalized or amino-functionalized solid phase A-OH or A-NH$_2$, or an activated form thereof, is reacted with a compound of the formula (VII)

(VII)

in which Y is the optionally branched spacer group which can optionally carry a protecting group, to give the derivative of the formula (VIII)

(VIII)

vi) the derivative of the formula (VIII) is then converted, after prior elimination of an optionally introduced protecting group, into a corresponding isothiocyanate, vii) the isothiocyanate is then coupled to the conjugate of the formula (VI) to give the thiourea of the formula (IX), and

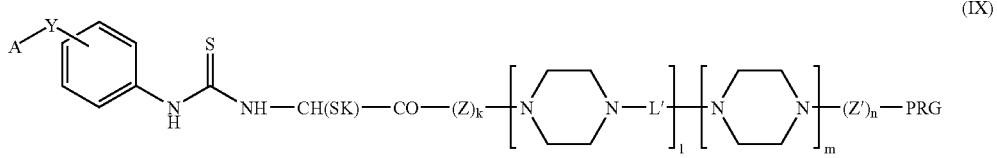

(IX)

viii) in an optional last step, protecting groups which are still present are eliminated, where appropriate, with it being possible to carry out the consecutive steps v) and vi) at any arbitrary time prior to step vii).

In all the reaction steps, it is possible to use protecting groups which can be reversibly eliminated, as are customary in peptide chemistry. A protecting group SG can be retained or detached at the same time as the Boc protecting group or be detached in a separate step. Examples of suitable protecting groups are the Boc protecting group, which can be cleaved using trifluoroacetic acid, or the Fmoc protecting group, which can be cleaved using piperidine or morpholine. Other suitable protecting groups, and the appropriate methods for introducing and eliminating them, have been described, for example, in Jakubke/Jeschkeit; Aminosäuren, Peptide, Proteine [Amino acids, peptides and proteins]; Verlag Chemie 1982 or in Houben-Weyl, Methoden der Organischen Chemie [Methods of organic chemistry], Georg Thieme Verlag Stuttgart, fourth edition; volumes 15.1 and 15.2, edited by E. Wünsch.

The affinity tags can also be optionally constructed in the reverse sequence, with the Boc protecting group being first of all detached from derivatives of the formula (IV). The unblocked compounds are then reacted with isothiocyanates which are correspondingly generated from (VIII) to give compounds of the formula protein-reactive group or the activated precursor of the derivative of a protein-reactive group

U-PRG (V)

is carried out in the last step, with compounds of the formula (IX) being obtained in this way as well.

The invention consequently also relates to a process for preparing a compound as claimed in claim 1 in which process i) a protected intermediate of the formula (III)

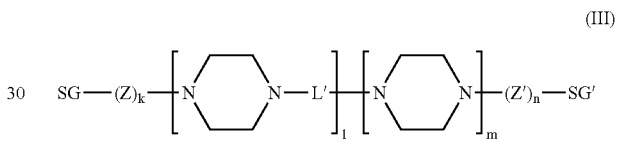

in which SG and SG' are two orthogonal protecting groups, is prepared, ii) the protecting group SG is first of all detached from the intermediate of the formula (III) and, after that, another amino acid derivative, which carries a protecting group SG, which is identical to, or different from, the detached protecting group, on the α-amino function, is attached, with a derivative of the formula (IV),

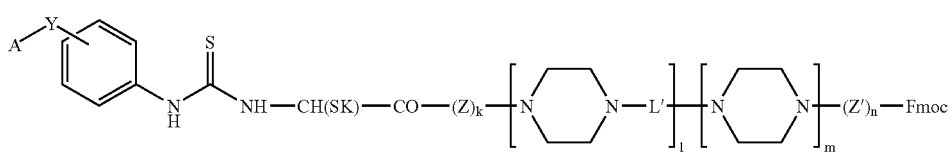

(X)

After the Fmoc protecting group has been detached using piperidine, the coupling with the derivative of a

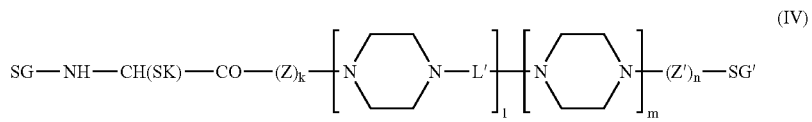

(IV)

in which SK is the side chain of an amino acid,
being obtained, iii) the terminal protecting group SG is detached, with a conjugate of the formula (VI')

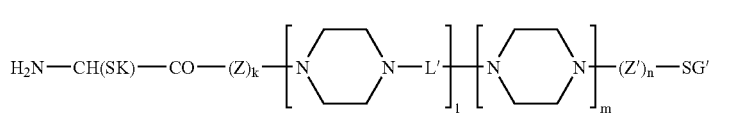

(VI')

being obtained, iv) an affinity ligand A-OH or A-NH$_2$, or a hydroxyl-functionalized, carboxyl-functionalized or amino-functionalized solid phase A-OH or A-NH$_2$, or an activated form thereof, is reacted with a compound of the formula (VII)

(VII)

in which Y is the optionally branched spacer group which can optionally carry a protecting group, to give the derivative of the formula (VIII)

(VIII)

v) the derivative of the formula (VIII) is then converted, after the prior elimination of an optionally introduced protecting group, into a corresponding isothiocyanate, vi) the isothiocyanate is then coupled to the conjugate of the formula (VI') to give the thiourea of the formula (X'), and and viii) in an optional last step, protecting groups which may still be present are eliminated, with it being possible to carry out the consecutive steps iv) and v) at any arbitrary time prior to step vi).

The reactions can be carried out under a variety of pressure and temperature conditions, for example at from 0.5 to 2 bar, and preferably under normal pressure, and, respectively, at from −30 to +100° C. and preferably at from −10 to +80° C., in suitable solvents, such as dimethylformamide (DMF), tetrahydrofuran (THF), dichloromethane, chloroform, lower alcohols, acetonitrile, dioxane or water, or in mixtures of said solvents. As a rule, preference is given to reactions in DMF, dichloromethane, THF, dioxane/water or THF/dichloromethane, at room temperature or while cooling with ice and under normal pressure.

Consequently, the described types of affinity tags can be prepared in a variety of ways, both linearly and also by means of coupling blocks which have already been prefabricated. The modular construction principle makes possible a large number of conceivable combinations and consequently, when the isotope-labeled modules are selected appropriately, arbitrary specification of the nature, number and location of the isotope labels. Only by using $^{13}$C and $^{15}$N isotopes in molecules of the same construction is it possible to obtain an arbitrary number, preferably up to 30, isotope labelings. This thereby opens the way to the simultaneous analysis of several, preferably up to 4, complex proteome samples.

EXAMPLES 42 affinity tags of the formula (II), in which A is the acyl residue of biotin, and one affinity tag of the formula (II) in

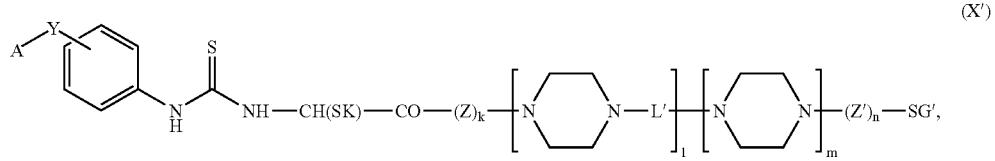

(X')

vii) after the protecting group SG' has been detached from the thiourea of the formula (X'), the latter is reacted with the derivative of a protein-reactive group or the activated precursor of the derivative of a protein-reactive group of the formula (V)

U-PRG (V)

in which U is a group which enables PRG to be linked to Z' or, where appropriate, to another end group of L, which A is an amino group-functionalized polymeric support (Example 42), were prepared and are assembled in the following table. In this connection, Z and Z', insofar as they are present, and with the exception of Z in Example 26 and Z' in Example 43, represent the respective glycine residue such that it is only the value of k and n, respectively, which are in each case indicated, with the groups $Z^1$ and $Z^2$ being indicated and defined in the case of $(Z)_k$ in Example 26 and $(Z')_n$ in Example 43, respectively.

| | S | | $(Z)_k$ | $[(C_4H_8N_2)L']_l$ | | $[C_4H_8N_2]_m$ | $(Z')_n$ | |
|---|---|---|---|---|---|---|---|---|
| Ex. | Y | SK of | k | l | L' | m | n | PRG |
| 1 | NHCH$_2$ | Gly | 1 | 0 | — | 1 | 1 | q = 0 |
| 2 | NHCH$_2$ | Gly | 1 | 0 | — | 1 | 1 | q = 1 |
| 3 | NHCH$_2$ | His | 1 | 0 | — | 1 | 1 | q = 0 |
| 4 | NHCH$_2$ | Asp | 1 | 0 | — | 1 | 1 | q = 1 |
| 5 | NHCH$_2$ | Val | 1 | 0 | — | 1 | 1 | q = 1 |
| 6 | NHCH$_2$ | Pro | 1 | 0 | — | 1 | 1 | q = 1 |
| 7 | NHCH$_2$ | D-Val | 1 | 0 | — | 1 | 1 | q = 1 |
| 8 | NHCH$_2$ | Gly | 0 | 0 | — | 1 | 1 | q = 1 |
| 9 | NHCH$_2$ | Asn | 1 | 0 | — | 1 | 1 | q = 1 |
| 10 | NH(CH$_2$)$_2$—NHCO | Gly | 1 | 0 | — | 1 | 1 | q = 1 |
| 11 | NH | Gly | 1 | 0 | — | 1 | 1 | q = 1 |
| 12 | NHCH$_2$ | D-Val | 0 | 0 | — | 1 | 1 | q = 1 |
| 13 | NH | Gly | 1 | 0 | — | 1 | 1 | q = 4 |
| 14 | NH | Gly | 1 | 0 | — | 1 | 1 | q = 2 |
| 15 | NH | Gly | 1 | 0 | — | 1 | 1 | AA |
| 16 | NH | Gly | 1 | 0 | — | 1 | 1 | r = 1 |
| 17 | NH | Gly | 1 | 1 | L$^1$ | 1 | 1 | q = 1 |
| 18 | NH | Gly | 1 | 2 | L$^1$ | 1 | 1 | q = 2 |
| 19 | NH | Gly | 1 | 1 | CO—CO | 1 | 1 | q = 1 |
| 20 | NH | Gly | 1 | 1 | L$^2$ | 1 | 1 | q = 1 |
| 21 | NH | His | 1 | 0 | — | 1 | 1 | q = 2 |
| 22 | NH | Glu | 1 | 0 | — | 1 | 1 | q = 2 |
| 23 | NH | His | 1 | 0 | — | 1 | 1 | q = 2 |
| 24 | NHCH$_2$ | Gly | 0 | 0 | — | 1 | 1 | q = 2 |
| 25 | NHCH$_2$ | His | 0 | 0 | — | 1 | 1 | q = 2 |
| 26 | NHCH$_2$ | Gly | Z$^1$ | 0 | — | 1 | 1 | q = 2 |
| 27 | NH | Gly | 0 | 1 | L$^1$ | 1 | 1 | q = 2 |
| 28 | NHCH$_2$ | Gly | 0 | 1 | CO—CO | 1 | 2 | q = 2 |
| 29 | NHCH$_2$ | Gly | 0 | 1 | L$^3$ | 1 | 1 | q = 2 |
| 30 | NHCH$_2$ | Gly | 0 | 1 | L$^4$ | 1 | 1 | q = 2 |
| 31 | NH | Gly | 0 | 1 | L$^4$ | 1 | 1 | q = 2 |
| 32 | NH | His | 0 | 1 | CO—CO | 1 | 2 | q = 2 |
| 33 | NHCH$_2$ | His | 0 | 1 | CO—CO | 1 | 2 | q = 2 |
| 34 | NHCH$_2$ | Gly | 0 | 1 | CO—CO | 1 | 2 | q = 4 |
| 35 | NH | Gly | 0 | 1 | CO—CO | 1 | 2 | q = 4 |
| 36 | NHCH$_2$ | His | 0 | 1 | CO—CO | 1 | 2 | q = 4 |
| 37 | NH | His | 0 | 1 | CO—CO | 1 | 2 | q = 4 |
| 38 | NH | Gly | 0 | 1 | CO—CO | 1 | 2 | q = 2 |
| 39 | NH | Gly | 0 | 1 | CO—CO | 1 | 2 | q = 2 |
| 40 | NH | Gly | 0 | 1 | CO—CO | 1 | 2 | q = 2 |
| 41 | NH | Gly | 0 | 1 | CO—CO | 1 | 2 | q = 2 |
| 42 | COCH$_2$ | Gly | 0 | 1 | CO—CO | 1 | 2 | q = 2 |
| 43 | NHCH$_2$ | Gly | 0 | 0 | — | 1 | Z$^2$ | q = 3 |
| 44 | NHCH$_2$ | Gly | 0 | 0 | — | 1 | Z$^3$ | q = 2 |
| 45 | NHCH$_2$ | Gly | 0 | 0 | — | 1 | Z$^3$ | q = 4 |
| 46 | NH | Gly | 0 | 0 | — | 1 | Z$^3$ | q = 2 |
| 47 | NH | Gly | 0 | 0 | — | 1 | Z$^3$ | q = 4 |
| 48 | COCH$_2$ | Gly | 1 | 0 | — | 1 | 1 | q = 2 |

L$^1$ = CO—CH$_2$—NH—CO;
AA = COCHCH$_2$;
Z$^1$ = NH—(CH$_2$)$_2$—CO;
L$^2$ = CO—CH$_2$—NH—CO—NH—CH$_2$—CO;
L$^3$ = (CH$_2$)$_3$—NH—CO—CO—NH—(CH$_2$)$_3$;
L$^4$ = (CH$_2$)$_2$—CO;

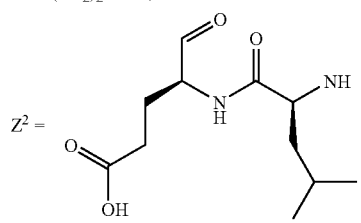

-continued

| | S | (Z)$_k$ | [(C$_4$H$_8$N$_2$)L']$_l$ | [C$_4$H$_8$N$_2$]$_m$ | (Z')$_n$ | |
|---|---|---|---|---|---|---|
| Ex. | Y | SK of | k | l | L' | m | n | PRG |

Z$^3$ = [structure: aldehyde-leucyl-leucine-NH fragment]

Abbreviations employed:
Boc tert-butoxycarbonyl
DIEA diisopropylethylamine (Hünig's base)
DMAP dimethylaminopyridine
DMF dimethylformamide
DMSO dimethyl sulfoxide
EI electron impact ionization
ESI electrospray ionization
Fmoc fluorenyl-9-methoxycarbonyl
HPLC high performance liquid chromatography
MALDI matrix-assisted laser desorption ionization
MS mass spectroscopy
MTBE methyl tert-butyl ether
quant. quantitative (i.e. complete) reaction
RP reverse phase
RT room temperature
TCEP tris(carboxyethyl)phosphine
TFA trifluoroacetic acid
THF tetrahydrofuran
TLC thin layer chromatography
(v/v) indication of concentration in volume per volume
(w/v) indication of concentration in mass per volume Unless otherwise expressly indicated, the compositions of solvent and eluent mixtures are in each case given by the names of the components, separated by "/" and, after that, the relative parts by volume. Thus, for example, "acetonitrile/water 10/1" means a mixture of acetonitrile and water in the ratio by volume of 10 to 1.

Eluents which are preferably employed (referred to by indicating [1] etc.):
[1] acetonitrile/water 10/1
[2] acetonitrile/water 20/1
[3] dichloromethane/methanol 97.5/2.5
[4] acetonitrile/water/glacial acetic acid 10/1/0.1
[5] acetonitrile/water/glacial acetic acid 5/1/0.2
[6] acetonitrile/water/glacial acetic acid 10/3/1.5
[7] dichloromethane/methanol/aqueous ammonia (17%) 15/2/0.2
[8] acetonitrile/water/glacial acetic acid 10/5/3
[9] dichloromethane/methanol/aqueous ammonia (17%) 15/4/0.5

For the preparation, which is described below, of the exemplary affinity tags, the biotin derivatives of the starting compound series 1 and the piperazine derivatives of the starting compound series 2 were prepared first of all. The piperazine derivatives were then converted into the intermediates of the intermediate series 1 to 3. Finally, these intermediates were reacted with the biotin derivatives to give corresponding affinity tags.

Starting Compound Series 1: Biotin Derivatives

SC.1.1

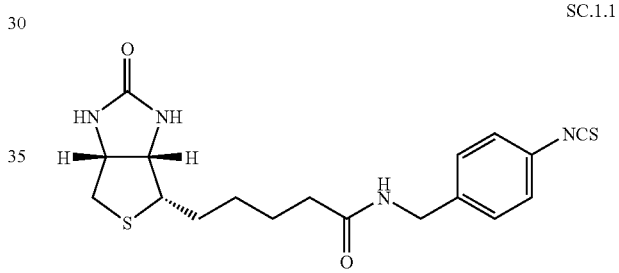

1 g (4.09 mmol) of biotin, 500 mg (4.09 mmol) of 4-aminobenzylamine as well as 830 mg (6.14 mmol) of 1-hydroxy-1H-benzotriazole, 942 mg (4.91 mmol) of N-(3-dimethylaminopropyl)-N'-ethylcarbodiimide hydrochloride and 1587 mg of ethyldiisopropylamine were added together in 40 ml of DMF. The mixture was stirred overnight at room temperature and concentrated, and the residue was purified by flash chromatography on silica gel (elution mixture: dichloromethane/meth-anol/aqueous ammonia (17%) 15/3/0.3). The appropriate fractions were combined and the solvent was evaporated off in vacuo. The residue was stirred up with diethyl ether and filtered off with suction. 1097 mg (77%) of the intermediate were obtained [TLC: dichloromethane/methanol/aqueous ammonia (17%) 15/4/0.5: $R_f$=0.58] [ESI-MS: m/e=349 (M+H)$^+$].

600 mg (1.72 mmol) of this intermediate were dissolved in 40 ml of dioxane/water 1/1, after which 298 mg (2.58 mmol) of thiophosgene and 890 mg of ethyldiisopropylamine were added. The mixture was stirred at room temperature for 10 min and then concentrated. The target product SC.1.1 was precipitated with diethyl ether from dichloromethane/methanol.

Yield: 616 mg (92%) [TLC: $R_f$=0.56[5]] [ESI-MS: m/e=391 (M+H)$^+$].

SC.1.2

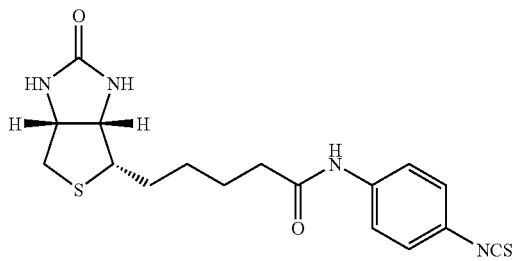

Mono-Fmoc-protected p-phenylenediamine was prepared using standard methods as described, for example, in Houben-Weyl; Methoden der Organischen Chemie [Methods of organic chemistry]; fourth edition; volume XV parts 1 and 2; Georg Thieme Verlag Stuttgart 1974, or in Hans-Dieter Jakubke and Hans Jeschkeit: Aminosäuren, Peptide, Proteine [Amino acids, peptides and proteins]; Verlag Chemie, Weinheim 1982.

200 mg (0.82 mmol) of biotin were taken up in 10 ml of dichloromethane and 974 mg (8.2 mmol) of thionyl chloride were added. After the mixture had been stirred for 1 h, it was concentrated and the residue was subsequently distilled twice with dichloromethane.

The resulting acid chloride (0.81 mmol) was taken up in 30 ml of dichloromethane, after which 387 mg (4.9 mmol) of pyridine and 242 mg (0.55 mmol) of mono-Fmoc-protected p-phenylenediamine were added. The mixture was stirred at RT for 2 days and the precipitated product was filtered off. This resulted in 300 mg (99%) of the intermediate, which was used in the next reaction step without any further purification [TLC: $R_f$=0.5[1)]].

The crude product was taken up in 5 ml of DMF and 500 μl of piperidine were added. After the mixture had been stirred at room temperature for 15 min, it was concentrated and the residue was purified by flash chromatography on silica gel (elution mixture [7)]). The appropriate fractions were combined, the solvent was removed and the residue was dried in vacuo. 69 mg (39%) of the deprotected intermediate were obtained.

65 mg (0.19 mmol) of this intermediate were dissolved in 10 ml of dioxane/water 1/1, after which 33 mg (0.29 mmol) of thiophosgene and 100 mg of ethyldiisopropylamine were added. The mixture was stirred at room temperature for 10 min and concentrated. The target product SC.1.2 was precipitated with diethyl ether from dichloromethane/methanol.

Yield: 65 mg (89%) [TLC: $R_f$=0.43[1)]] [ESI-MS: m/e 377 (M+H)[+]].

hydrochloride of the mono-Fmoc protected ethylenediamine, as well as 739 mg (5.47 mmol) of 1-hydroxy-1H-benzotriazole and 839 mg (4.38 mmol) of N-(3-dimethylaminopropyl)-N'-ethylcarbodiimide hydrochloride, were added. The mixture was stirred at room temperature for 2 h, after which it was concentrated and the residue was taken up in 200 ml of dichloromethane. It was then extracted three times by shaking with 200 ml of sodium hydrogencarbonate solution. The organic phase was concentrated and the residue was purified by flash chromatography on silica gel (eluent: acetonitrile). The appropriate fractions were combined and the solvent was evaporated off in vacuo and the residue was dried. This resulted in 639 mg (59%) of the intermediate [TLC: $R_f$=0.68 [2)]].

400 mg (1 mmol) of the intermediate were taken up in 10 ml of DMF, after which 500 μl of piperidine were added. After the mixture had been stirred at room temperature for 15 min, it was concentrated and the residue was purified by flash chromatography on silica gel (elution mixture: dichloromethane/methanol/aqueous ammonia (17%) 15/4/0.5). The appropriate fractions were combined, the solvent was removed and the residue was dried in vacuo. This resulted in 147 mg (82%) of the deprotected intermediate [TLC: $R_f$=0.18 [5)]].

191 mg (0.78 mmol) of biotin were taken up in 10 ml of DMF, after which 158 mg (1.17 mmol) of 1-hydroxy-1H-benzotriazole and 180 mg (0.94 mmol) of N-(3-dimethylaminopropyl)-N'-ethylcarbodiimide hydrochloride were added. The mixture was stirred at RT for 10 min and 303 mg of ethyldiisopropylamine and 140 mg (0.78 mmol) of the deprotected intermediate were added. The mixture was then stirred once again at RT for 6 h, after which it was concentrated and the crude product was precipitated with diethyl ether from dichloromethane. The residue was separated off and purified by flash chromatography on silica gel (elution mixture: dichloromethane/methanol/aqueous ammonia (17%) 15/3/0.3). The appropriate fractions were combined and the solvent was evaporated off in vacuo and the residue was dried. This resulted in 222 mg (70%) of the intermediate [TLC: dichloromethane/methanol/aqueous ammonia (17%) 15/4/0.5: $R_f$=0.47].

200 mg (0.54 mmol) of this intermediate were dissolved in 15 ml of dioxane/water 1/1, after which 94 mg (0.81 mmol) of thiophosgene and 210 mg of ethyldiisopropylamine were added. The mixture was stirred at room temperature for 15 min and then concentrated. The target product was precipitated with diethyl ether from dichloromethane/methanol.

Yield: 230 mg (95%) [TLC: $R_f$=0.44 [5)]][ESI-MS: m/e=448 (M+H)[+]].

Starting Compound Series 2: Piperazine Derivatives

SC.1.3

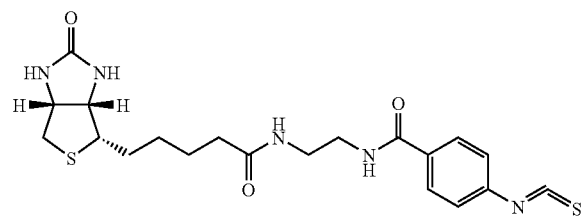

500 mg (3.65 mmol) of 4-aminobenzoic acid were taken up in 20 ml of DMF, after which 872 mg (2.73 mmol) of the

SC.2.1

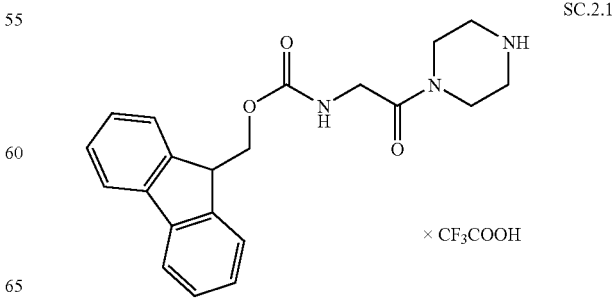

× CF$_3$COOH 3.85 g (13 mmol) of Fmoc-glycine, as well as 2.19 g (16.2 mmol) of 1-hydroxy-1H-benzotriazole and 2.48 g (13 mmol) of N-(3-dimethylaminopropyl)-N'-ethylcarbodiimide hydrochloride were added together in 80 ml of DMF and the mixture was stirred at RT for 30 min. After that, 2.01 g (10.8 mmol) of Boc-piperazine, dissolved in 40 ml of DMF, were added dropwise and 2.8 g of ethyldiisopropylamine were also added. The mixture was stirred at RT for 2 h and concentrated. The residue was taken up in dichloromethane and shaken twice with water. The organic phase was separated off and concentrated and the residue was purified by flash chromatography on silica gel (eluent: acetonitrile). The appropriate fractions were combined, the solvent was evaporated off in vacuo and the residue was dried. This resulted in 3.91 g (78%) of the intermediate [TLC: $R_f$=0.58 $^{2)}$].

3.9 g (8.4 mmol) of this intermediate were taken up in 50 ml of dichloromethane, after which 25 ml of TFA were added. After the mixture had been stirred at room temperature for 30 min, it was concentrated and the residue was precipitated with diethyl ether from dichloromethane, filtered off and dried. 4.8 g (93%) of the target product SC.2.1 were obtained [TLC: $R_f$=0.31 $^{5)}$].

SC.2.2

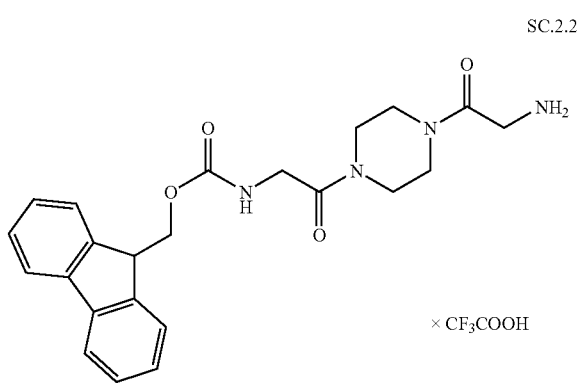

× CF₃COOH 0.53 g (3 mmol) of Boc-glycine, as well as 0.51 g (3.75 mmol) of 1-hydroxy-1H-benzotriazole and 0.58 g (3 mmol) of N-(3-dimethylaminopropyl)-N'-ethylcarbodiimide hydrochloride were added together in 40 ml of DMF and the mixture was stirred at RT for 30 min. Subsequently, 1 g of ethyldiisopropylamine was added, after which 1.2 g (2.5 mmol) of the product SC.2.1 were added slowly. The mixture was stirred overnight at RT and concentrated. The residue was taken up in dichloromethane and extracted twice by shaking with sodium hydrogencarbonate solution. The organic phase was separated off and concentrated and the residue was purified by flash chromatography on silica gel (eluent: acetonitrile/water 30/1). The appropriate fractions were combined, the solvent was evaporated off in vacuo and the residue was dried. This resulted in 760 mg (58%) of the intermediate [TLC: $R_f$=0.6 $^{2)}$].

760 mg (1.45 mmol) of this intermediate were taken up in 10 ml of dichloromethane, after which 5 ml of TFA were added. After the mixture had been stirred at room temperature for 30 min, it was concentrated and the residue was precipitated with diethyl ether from dichloromethane, filtered off and dried. 780 mg of the target product SC.2.2 were obtained (quantitative conversion) [TLC: $R_f$=0.4 $^{5)}$].

SC.2.3

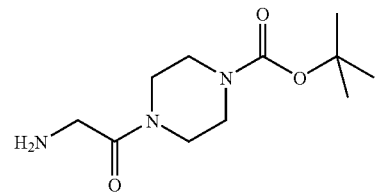

3.85 g (13 mmol) of Fmoc-glycine, and also 2.19 g (16.2 mmol) of 1-hydroxy-1H-benzotriazole and 2.48 g (13 mmol) of N-(3-dimethylaminopropyl)-N'-ethylcarbodiimide hydrochloride, were added together in 80 ml of DMF and the mixture was stirred at RT for 30 min. After that, 2.01 g (10.8 mmol) of Boc-piperazine, dissolved in 40 ml of DMF, were added dropwise and 2.8 g of ethyldiisopropylamine were also added. The mixture was stirred at RT for 2 h and concentrated. The residue was taken off in dichloromethane and extracted twice by shaking with water. The organic phase was separated off and concentrated and the residue was purified by flash chromatography on silica gel (eluent: acetonitrile). The appropriate fractions were combined, the solvent was evaporated off in vacuo and the residue was dried. This resulted in 3.91 g (78%) of the intermediate [TLC: $R_f$=0.58 $^{2)}$].

730 mg (1.57 mmol) of this intermediate were dissolved in 5 ml of DMF after which 500 µl of piperidine were added. After the mixture had been stirred at RT for 15 min, it was concentrated and the residue was purified by flash chromatography on silica gel (eluent $^{7)}$). The appropriate fractions were combined and the solvent was evaporated off in vacuo. The residue was stirred up with diethyl ether/petroleum ether 1/1, after which it was filtered off and dried. This resulted in 222 mg (58%) of the target product SC.2.3 [TLC: $R_f$=0.18 $^{7)}$].

SC.2.4: Piperazine-$^{13}C_4$

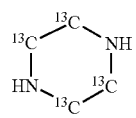

Standard conditions were used to protect the amino group of glycine-$^{13}C_2$ with the t-butoxycarbonyl (Boc) protecting group.

Subsequently, 1.175 g (3.83 mmol) of Boc-glycine-$^{13}C_2$ were dissolved in dioxane/water 1/1, after which 2.5 g (7.67 mmol) of cesium carbonate were added. The mixture was lyophilized, after which the product was taken up in DMF and 2.72 g (19.17 mmol) of iodomethane were then added to it. After the mixture had been stirred at RT for 2 h, it was concentrated and the residue was partitioned between dichloromethane and water. The organic phase was washed once again with water, after which it was dried over sodium sulfate and concentrated. 530 mg (72%) of the methyl ester were obtained.

525 mg (2.75 mmol) of the Boc-protected methyl ester were then deprotected at the amino group with trifluoroacetic acid (yield: 506 mg; 90%).

Standard conditions were used to react the resulting product (500 mg) with Boc-glycine-$^{13}C_2$ to give the bilaterally protected dipeptide conjugate containing four $^{13}C$ atoms (yield: 452 mg; 74%).

The Boc group was once again detached from this intermediate using TFA (quantitative conversion).

475 mg (1.8 mmol) of this N-terminally unblocked, $^{13}C$-labeled dipeptide methyl ester trifluoroacetate were dissolved in 15 ml of methanol and 697 mg (5.4 mmol) of ethyldiisopropylamine were then added. The mixture was stirred at RT for 3 days, in connection with which the diketopiperazine was formed and precipitated out. It was filtered off, washed with methanol and dried under high vacuum (yield: 138 mg; 65%).

130 mg (1.1 mmol) of the $^{13}C$-labeled diketopiperazine were taken up in 40 ml of THF, under argon, and 284 mg (3.3 mmol) of THF-borane complex were added. The mixture was stirred under reflux for 12 h and a further 284 mg (3.3 mmol) of THF-borane complex were added. After a further 16 h of refluxing, the mixture was allowed to cool down and was quenched with 6 ml of 10% hydrochloric acid. The mixture was boiled for a further 30 min and then allowed to cool down; it was concentrated and the residue was subsequently distilled with dichloromethane/methanol. The residue was then washed with dichloromethane/methanol 4:1 and filtered off. 145 mg (81%) of the fourfold $^{13}C$-labeled piperazine SC.2.4 were obtained [TLC: acetonitrile/water/ glacial acetic acid 10/3/1.5: $R_f$=0.23] [EI-MS: m/z=90 (M)$^+$ radical ion].

SC.2.5: Piperazine-$^{15}N_2$-$^{13}C_4$

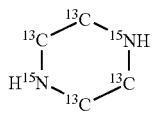

This building block was prepared from glycine-$^{13}C_2$—$^{15}N$ in analogy with SC.2.4.

All the intermediates and end products of the subsequent intermediate series and examples were prepared from these $^{13}C$-labeled and $^{13}C$- and $^{15}N$-labeled intermediates SC.2.4 and SC.2.5 in the same way as described for the unlabeled $^{12}C$- and $^{14}N$-analogs.

SC.2.6

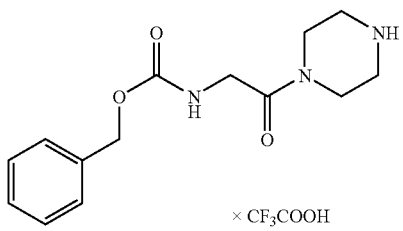

× CF$_3$COOH 7.459 g (24.36 mmol) of benzyloxycarbonylglycine-N-hydroxysuccinimide ester were added, together with 3 g (34.83 mmol) of piperazine and ethyldiisopropylamine, to 70 ml of DMF, and the mixture was stirred at RT for 2 h. The mixture was then concentrated and the residue was purified by flash chromatography on silica gel (eluent: dichloromethane/methanol/aqueous ammonia (17%) 15/2/0.2). The appropriate fractions were combined, the solvent was evaporated off in vacuo and the residue was dried. 4.04 g (60%) of the target compound were obtained [TLC: $R_f$= 0.26 $^{5)}$].

SC.2.7

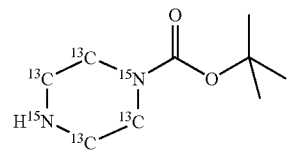

The Boc protecting group was introduced into the compound SC.2.5 in accordance with standard conditions and using 0.5 equivalent of Boc anhydride. Yield: 65% [TLC: $R_f$=0.22$^{5)}$].

SC.2.8

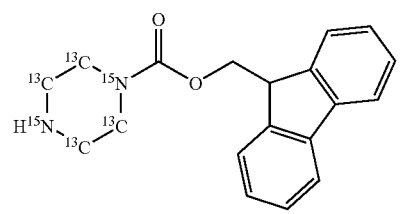

The Fmoc protecting group was initially introduced into the compound SC.2.7 in accordance with standard conditions and using Fmoc-Cl, and the Boc protecting group was then detached using trifluoroacetic acid. [TLC: $R_f$=0.32 $^{5)}$].

SC.2.9

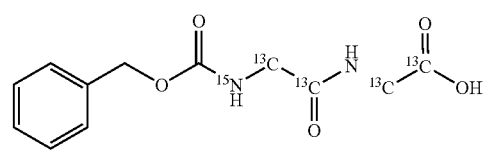

The protected dipeptide, carrying two $^{15}N$ and three $^{13}C$ labels, was prepared over 5 steps in accordance with standard conditions: first of all, the Z protecting group was introduced into [bis-$^{13}C$, $^{15}N$]-glycine using benzyloxycarbonyl chloride in dioxane/1N sodium hydroxide solution (yield: 47%). This amino acid derivative was coupled to [bis-$^{13}C$]-glycine methyl ester (intermediate in the preparation of SC.2.4) (yield: 77%) and, in the last step, the methyl ester was cleaved using 2N lithium hydroxide in methanol (yield: 75%). [TLC: $R_f$=0.25 $^{4)}$] [ESI-MS: m/e=272 (M+H)$^+$].

SC.2.10

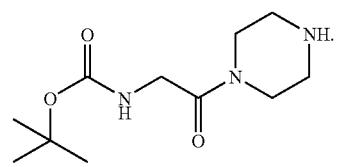

Preparation in analogy with SC.2.6 or from Fmoc-pip. [TLC: $R_f$=0.35 $^{5)}$].

Intermediate Series 1: Fully Protected Amino Acid-Flanked Piperazine Derivatives General Formula:

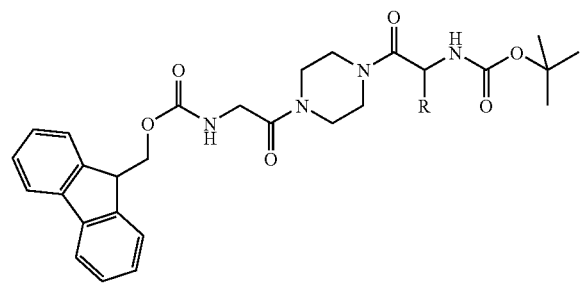

General Directions:

3 mmol of a Boc-protected amino acid derivative, as well as 0.51 g (3.75 mmol) of 1-hydroxy-1H-benzotriazole and 0.58 g (3 mmol) of N-(3-dimethylaminopropyl)-N'-ethylcarbodiimide hydrochloride, were together added to 40 ml of DMF and the mixture was stirred at RT for 30 min. 1 g of ethyl diisopropylamine was then added, after which 2.5 mmol of the products SC.2.1 or SC.2.2, dissolved in 40 ml of DMF, were added dropwise. The mixture was stirred overnight at RT and concentrated. The residue was taken up in dichloromethane and this mixture was extracted twice by shaking with sodium hydrogencarbonate solution. The organic phase was separated off and concentrated and the residue was purified either by precipitation from dichloromethane with diethyl ether or by flash chromatography on silica gel (eluent: acetonitrile/water 30/1). The appropriate fractions were combined, the solvent was evaporated off in vacuo and the residue was dried. The fully protected intermediates were obtained.

I.1.1 (R=H (Glycine Residue))
Starting compounds: Boc-glycine; SC.2.1
  Yield: 58% $R_f$=0.45 [1]

I.1.2 (R=D-Valine Residue)
Starting compounds: Boc-D-valine; SC.2.1
Purification: flash chromatography; Eluent: dichloromethane/methanol 98/2
  Yield: 76% $R_f$=0.3 [3]

Intermediate Series 2: Fully Protected Peptide-Flanked Piperazine Derivatives

General Formula:

I.2.1 (R=H (Glycine (Gly) Residue))
Starting compounds: Boc-glycine; SC.2.2
  Yield: 86% $R_f$=0.55 [1]

I.2.2 (R=Side Chain Boc-Protected Histidine (His) Residue)
Starting compounds: Bis-Boc-histidine-N-hydroxysuccinimide ester; SC.2.2
Special features: Instead of the EDCI/HOBT activation, the hydroxysuccinimide ester was used immediately in this case. Purification by precipitation.
  Yield: 85% $R_f$=0.47 [1]

I.2.3 (R=Side Chain Tert-Butyl Ester-Protected Aspartic Acid (Asp) Residue)
Starting compounds: γy-tert-butyl Boc-aspartate; SC.2.2
Special features: purification by precipitation.
  Yield: 68% $R_f$=0.66 [1]

I.2.4 (R=Valine (Val) Residue)
Starting compounds: Boc-valine; SC.2.2
Special features: purification by precipitation.
  Yield: 79% $R_f$=0.64 [4]

I.2.5 (R=Asparagine (Asn) Residue)
Starting compounds: Boc-asparagine; SC.2.2
Special features: purification by flash chromatography using eluent [2].
  Yield: 66% $R_f$=0.47 [1]

I.2.6 (R=Proline (Pro) Residue)
Starting compounds: Boc-proline-N-hydroxysuccinimide ester; SC.2.2
Special features: The activated amino acid derivative was used instead of EDCI/HOBT. Purification by flash chromatography using acetonitrile/water 15/1.
  Yield: 98% $R_f$=0.55 [5]

I.2.7 (R=D-Valine (D-Val) Residue)
Starting compounds: Boc-D-valine; SC.2.2
Special features: purification by flash chromatography using acetonitrile/water 30/1.
  Yield: 80% $R_f$=0.64 [1]

I.2.8 (R=β-Alanine Residue)
Starting compounds: Boc-p-alanine; SC.2.1
Special features: SC.2.1 was first of all reacted with Boc-β-analine and the Boc group was then detached; finally, Boc-glycine was attached.
  Yield: 15% over 3 steps $R_f$=0.45 [7]

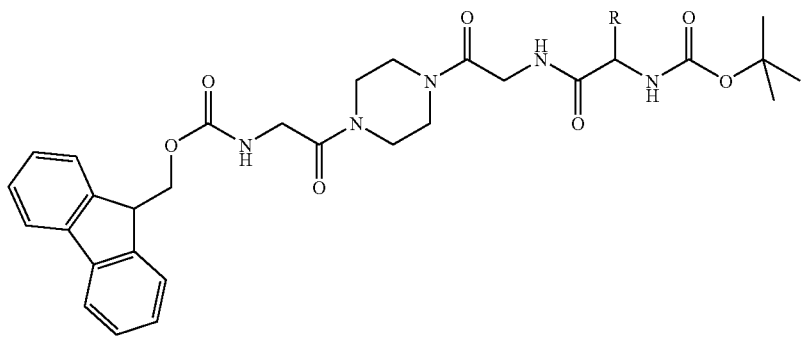

The products of the intermediate series 2 were prepared in accordance with the same general directions as previously described for the intermediate series 1.

I.2.9 (R=Tert-Butyl Ester-Protected Glutamic Acid Residue)
Starting compounds: γ-tert-butyl Boc-glutamate; SC.2.2
  Yield: 98% $R_f$=0.75 [1]

Intermediate Series 3: Oligopiperazine Derivatives

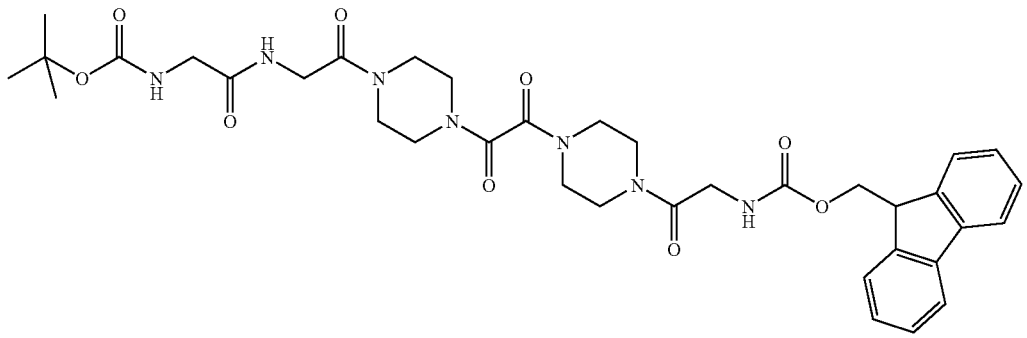

I.3.1

1438 mg (7.72 mmol) of Boc-piperazine were dissolved in 100 ml of dichloromethane, after which 500 mg (3.86 mmol) of oxalyl chloride and 625 µl of pyridine were added. After the mixture had been stirred at RT for 1 h, it was concentrated and the residue was stirred up twice with water. The remaining solid was sufficiently pure and was dried under high vacuum. 1230 mg (75%) were obtained.

Both Boc protective groups were detached from 1230 mg of this intermediate in accordance with standard conditions (yield: 1330 mg; quantitative conversion).

305 mg (1.31 mmol) of Boc-glycyc-glycine, as well as 242 mg (1.79 mmol) of 1-hydroxy-1H-benzotriazole and diimide hydrochloride were together added to 20 ml of DMF and the mixture was stirred at RT for 30 min. After that, 2270 mg (0.61 mmol) of the above-described intermediate were added, and 320 µl of ethyldiisopropylamine were also added. The mixture was stirred at RT for 2 h and concentrated. The residue was taken up in dichloromethane and this solution was extracted twice by shaking with water. The organic phase was separated off, dried over sodium sulfate and concentrated. The residue was then precipitated with diethyl ether from dichloromethane/methanol 1/1. The precipitate was filtered off and dried under high vacuum. This resulted in 195 mg (44%) of the intermediate I.3.1 [TLC: $R_f$=0.52 [4]].

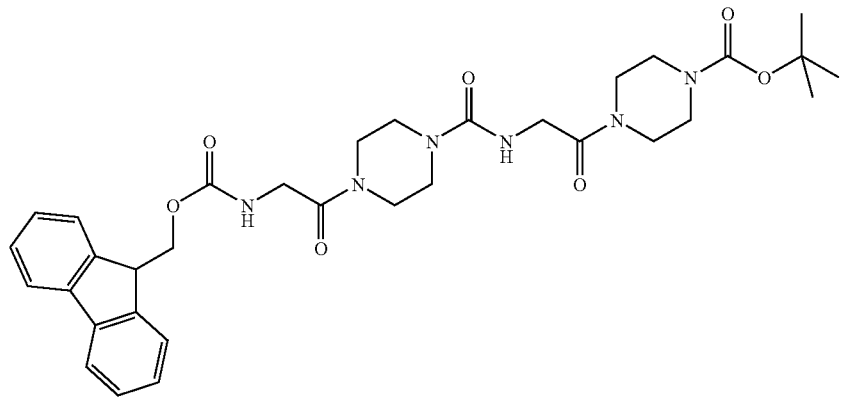

I.3.2

275 mg (1.43 mmol) of N-(3-dimethylaminopropyl)-N'-ethylcarbodiimide hydrochloride were together added to 25 ml of DMF and the mixture was stirred at RT for 30 min. After that, 543 mg (1.2 mmol) of the bilaterally deprotected intermediate, dissolved in 5 ml of DMF, were added dropwise and 625 µl of ethyldiisopropylamine were also added. The mixture was stirred at RT for 1 h and then concentrated. The residue was purified by flash chromatography on silica gel (eluent [5]). The appropriate fractions were combined, the solvent was evaporated off in vacuo and the residue was precipitated with diethyl ether from dichloromethane. The precipitate was filtered off and dried under high vacuum. 276 mg (53%) of the intermediate were obtained [TLC: $R_f$=0.32 [5]].

182 mg (0.61 mmol) of Fmoc-glycine, as well as 124 mg (0.92 mmol) of 1-hydroxy-1H-benzotriazole and 141 mg (0.74 mmol) of N-(3-dimethylaminopropyl)-N'-ethylcarbo- 30 mg (0.123 mmol) of the starting compound SC.2.3 were dissolved in dichloromethane, after which 25 mg (0.123 mmol) of 4-nitrophenyl chloroformate were added. 172 µl of diisopropylethylamine were added after the mixture had been stirred at RT for 30 min, and 59 mg (0.123 mmol) of the starting compound SC.2.1 were added after a further 30 min. The mixture was left to stand are RT overnight and then concentrated. The residue was taken up in 20 ml of dichloromethane and this solution was extracted by shaking with water. The organic phase was concentrated and the residue was purified by flash chromatography on silica gel (eluent [2]). The appropriate fractions were combined, the solvent was evaporated off in vacuo and the residue was taken up in dioxane/water 1/1 and lyophilized. This resulted in 55 mg (70%) of the intermediate I.3.2 [TLC: $R_f$=0.52 [1]] [ESI-MS: m/e=635 (M+H)$^+$].

I.3.3

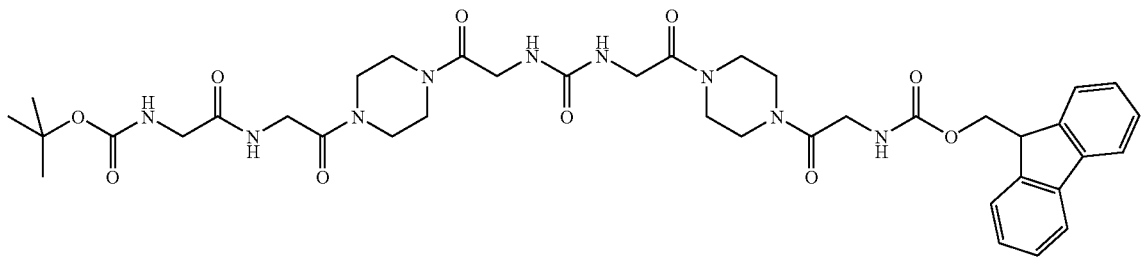

368 mg (0.63 mmol) of the intermediate I.2.1 were taken up in 5 ml of DMF and 500 µl of piperidine were added. After the mixture had been stirred at room temperature for 15 min, it was concentrated and the residue was purified by flash chromatography on silica gel (eluent: dichloromethane/methanol/aqueous ammonia (17%) 15/3/0.3). The appropriate fractions were combined, the solvent was evaporated off in vacuo and the residue was dried. 204 mg (90%) of the target product Boc-Gly-Gly-Pip-Gly were obtained [TLC: dichloromethane/methanol/aqueous ammonia (17%) 15/4/0.5: $R_f$=0.28].

70 mg (0.196 mmol) of this intermediate were dissolved in 18 ml of dichloromethane, after which 59 mg (0.294 mmol) of 4-nitrophenyl chloroformate were added. 273 µl of diisopropylethylamine were added after the mixture had been stirred at RT for 10 min and 105 mg (0.196.mmol) of the compound SC.2.2 were added after a further 2 h. The mixture was stirred overnight at RT. In connection with this, a solid precipitated out and was filtered off. 15 mg (10%) of the intermediate I.3.3 were obtained [TLC: $R_f$=0.18 [4)]] [ESI-MS: m/e=806 (M+H)+].

I.3.4

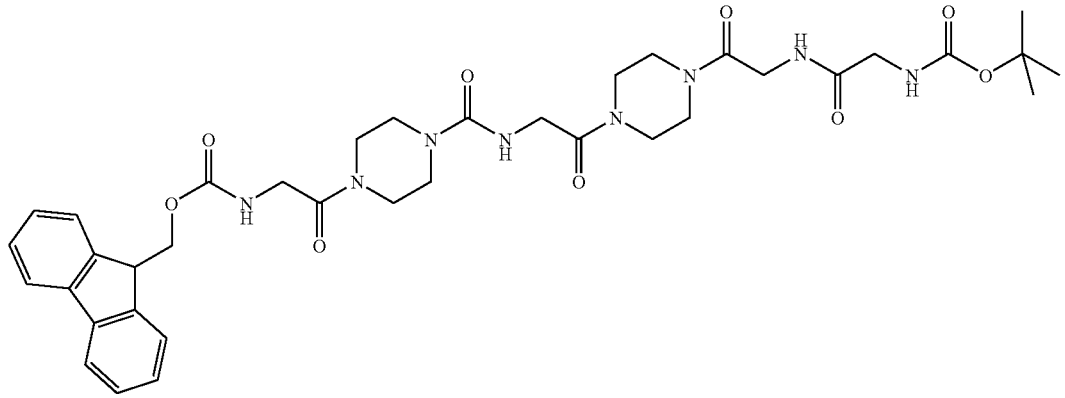

The Boc protecting group was first of all detached from the compound I.3.2 in a known manner. Boc-Gly-Gly-OH was then attached in the presence of EDCI/HOBT. The target product I.3.4 were obtained in a yield of 46% over 2 steps. [TLC: $R_f$=0.62 [5)]]

I.3.5

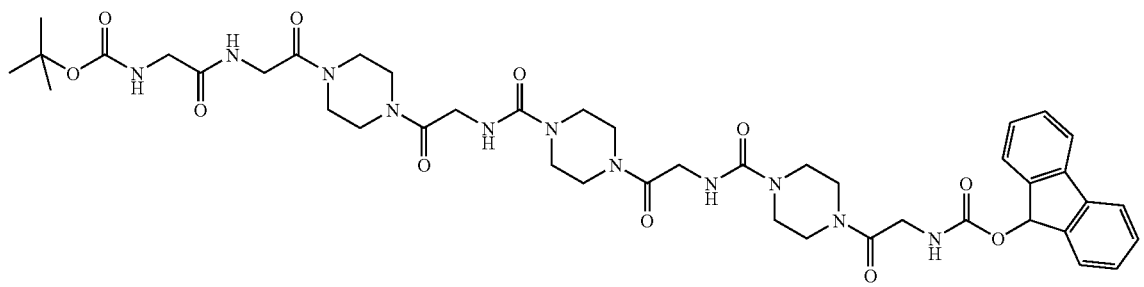

47 mg (0.193 mmol) of the starting compound SC.2.3 were dissolved in dichloromethane, after which 39 mg (0.193 mmol) of 4-nitrophenyl chloroformate were added. After the mixture had been stirred at RT for 10 min, 269 µl of diisopropylethylamine were added and the mixture was then stirred at RT for a further 20 min.

In parallel with this, the Boc protecting group was detached from the compound I.3.2 in a known manner. 125 mg (0.193 mmol) of the deprotected product were then added to the above mixture. The whole was stirred at RT for 4 h and then extracted with 10 ml of water. The organic phase was concentrated and the residue was precipitated with diethyl ether from dichloromethane/methanol 1/1. The precipitate was filtered off with suction and dried. This resulted in 124 mg (80%) of the intermediate [TLC: $R_f$= 0.2 [4)].

The Boc protecting group was once again detached from this intermediate in a known manner. Boc-Gly-Gly-OH was then attached in the presence of EDCI/HOBT. The target product was obtained in a yield of 35% over 2 steps [TLC: acetonitrile/water/glacial acetic acid 5/1/0.2: $R_f$=0.42] [ESI-MS: m/e=918 (M+H)$^+$].

1455 mg (11.46 mmol) of oxalyl chloride were dissolved in 2 ml of dichloromethane after which 100 mg (0.24 mmol) of Fmoc-piperidine in 10 ml of dichloromethane were added. After 1 h, the solvent was distilled off in vacuo and the residue was subsequently distilled using dichloromethane.

The residue was then once again taken up in 10 ml of dichloromethane and added to a solution of 44 mg (0.24 mmol) of Boc-piperidine and 187 mg of pyridine in 10 ml of dichloromethane. After the mixture had been stirred at RT for 1 h, the solvent was separated off in vacuo and the residue was purified by flash chromatography on silica gel (eluent: dichloromethane/methanol 97.5/2.5). The appropriate fractions were combined and the solvent was distilled off in vacuo. 74 mg (57%) of the fully protected intermediate were obtained [TLC: acetonitrile/water 20/1: $R_f$=0.6].

The Fmoc protecting group was detached from 72 mg (0.13 mmol) of this intermediate using piperidine in DMF.

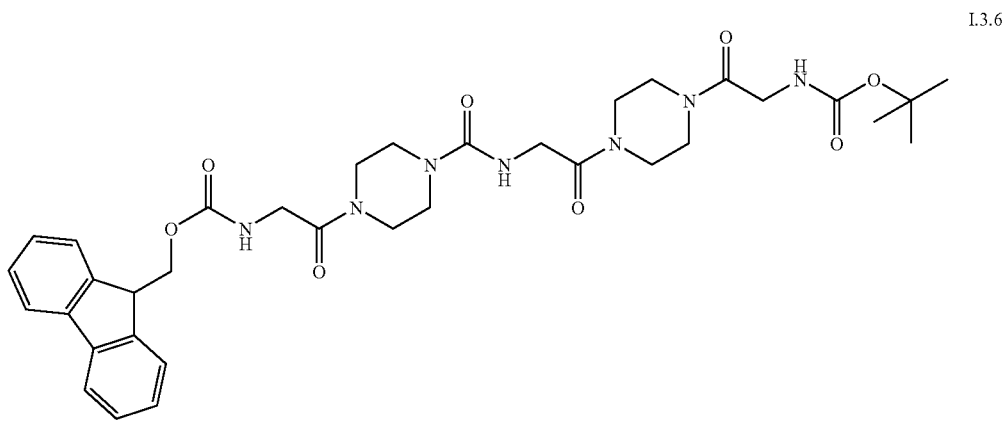

I.3.6

Proceeding from I.3.2, the following reactions were carried out in accordance with standard conditions: Boc elimination using trifluoroacetic acid in dichloromethane (yield: 87%), reaction with Boc-glycine-N-carboxylic acid anhydride (yield: 99%) [TLC: $R_f$=0.6 [1)].

In accordance with standard conditions using EDCI/HOBT, the deprotected product was coupled to benzyloxycarbonylglycylglycine, in the presence of ethyldiisopropylamine, to give the target product. Yield: 82% [TLC: $R_f$= 0.5 [4)].

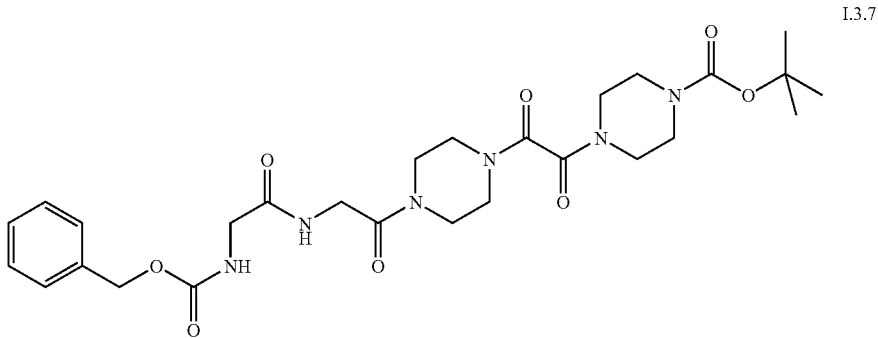

I.3.7

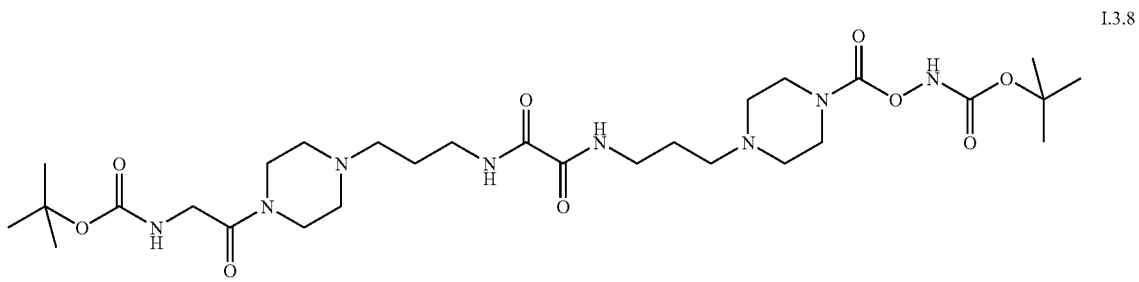

I.3.8

713 mg (2.93 mmol) of N-3-aminopropyl-N'-tert-butoxycarbonyl piperazine and 2.3 g of ethyldiisopropylamine were initially introduced in 100 ml of dichloromethane, after which 225 mg (1.78 mmol) of oxalyl chloride were added dropwise. After the mixture had been stirred at RT for 1 h, it was diluted with a further 100 ml of oxalyl chloride and then extracted three times by shaking with 5% strength sodium hydrogencarbonate solution. The organic phase was dried over sodium sulfate and concentrated. The residue was digested with diethyl ether and the product was filtered off. The mother liquor was precipitated once again with petroleum ether. 515 mg (54%) of the fully protected intermediate were obtained [TLC: $R_f$=0.3 [6)]].

The Boc protecting group was detached from the above using trifluoroacetic acid (quantitative reaction). In accordance with standard conditions using EDCI/HOBT, the deprotected product was then coupled to Boc-glycine, in the presence of ethyldiisopropylamine, to give the target product. Yield: 42% [TLC: $R_f$=0.61 [9)]] [ESI-MS: m/e=655 (M+H)+].

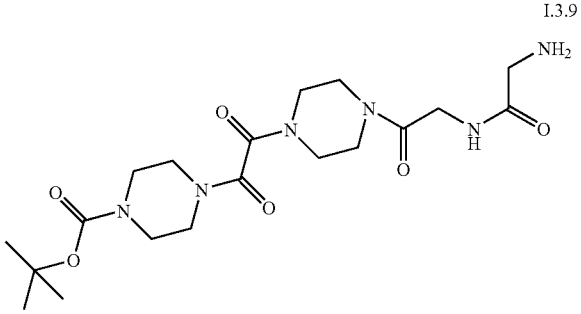

I.3.9

793 mg (1.38 mmol) of the compound from Example I.3.7 were dissolved in 40 ml of methanol and 15 ml of THF and hydrogenated over palladium/active charcoal (10% Pd). After 1 h, the catalyst was separated off and the solvent was evaporated. The residue was taken up in dioxane/water and lyophilized. This resulted in 512 mg (84%) of the target compound [TLC: $R_f$=0.17 [5)]].

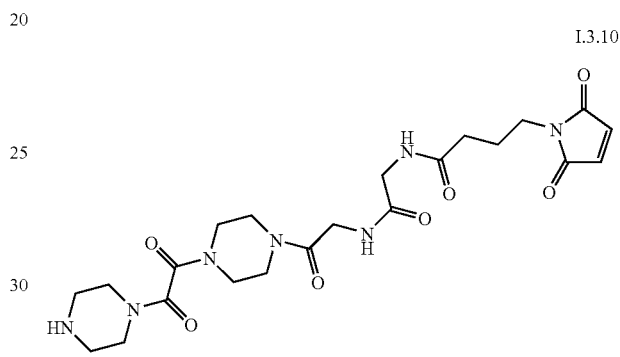

I.3.10

49.9 mg (0.272 mmol) of ω-maleimidobutyric acid, as well as 46 mg (0.34 mmol) of 1-hydroxy-1H-benzotriazole and 52 mg (0.272 mmol) of N-(3-dimethylaminopropyl)-N'-ethylcarbodiimide hydrochloride, were together added to 20 ml of DMF and the mixture was stirred at RT for 90 min. After that, 100 mg (0.227 mmol) of the compound from Example 1.3.9 were added, and 120 µl of ethyldiisopropylamine were also added. The mixture was stirred at RT for 6 h and concentrated. The residue was taken up in dichloromethane and this solution was extracted three times by shaking with water. The organic phase was separated off, dried over sodium sulfate and concentrated. The residue was then precipitated with diethylether from dichloromethane. The precipitate was filtered off and dried under high vacuum. 78 mg (yield: 57%) of the intermediate were obtained.

The Boc protecting group was detached from the above using trifluoroacetic acid in order to obtain the target compound (quantitative reaction) [TLC: $R_f$=0.28 [6)]].

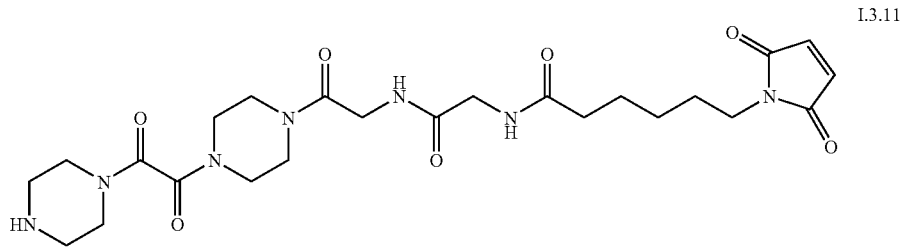

I.3.11

The preparation was effected in analogy with Example I.3.10, proceeding from I.3.9.
Yield: 72% [TLC: $R_f$=0.38 ⁶⁾].

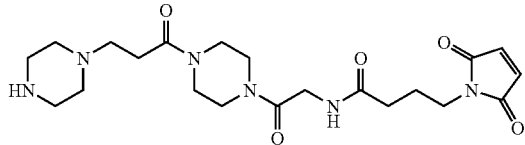

500 mg (1.94 mmol) of N-2-carboxyethyl-N'-tert-butoxy-carbonylpiperazine were coupled to 537 mg (1.94 mmol) of benzyloxycarbonylglycylpiperazine (compound SC.2.6) in accordance with standard conditions using EDCI/HOBT. 630 mg (yield: 63%) of the fully protected intermediate were obtained [TLC: $R_f$=0.4 ⁵⁾].

400 mg of the intermediate were hydrogenated in 40 ml of methanol and over palladium/active charcoal (10% Pd). After 3 h, the catalyst was separated off and the solvent was evaporated and the residue dried. 401 mg (yield: 95%) were obtained [TLC: $R_f$=0.2 ⁶⁾].

This intermediate was coupled to ω-maleimidobutyric acid as described in Example I.3.10 and using EDCI/HOBT. The Boc group was then detached using trifluoroacetic acid. The target compound was obtained in a yield of 46% over 2 steps [TLC: $R_f$=0.21 ⁸⁾].

I.3.13

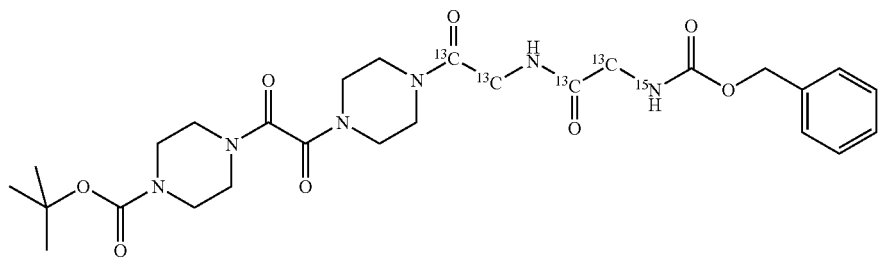

The preparation was effected in analogy to the example I.3.7 using the building blocks:
Fmoc-piperidine
Oxalyl chloride
Boc-piperidine
Compound from Example SC.2.9.
Yield: 52% over 4 steps [TLC: $R_f$=0.4 ⁷⁾][ESI-MS: m/e=580 (M+H)⁺].

I.3.14

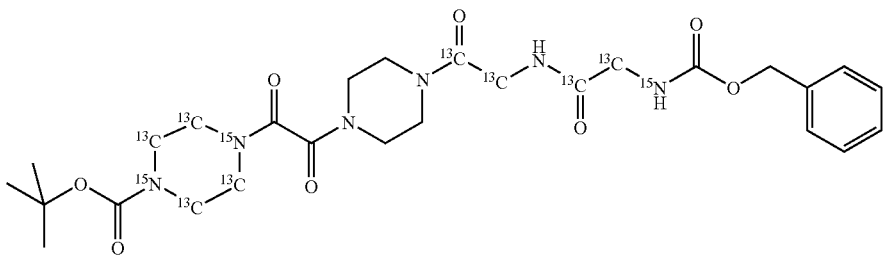

The preparation was effected in analogy with the Example I.3.7 using the building blocks:
Fmoc-piperidine
Oxalyl chloride
Compound from Example SC.2.7
Compound from Example SC.2.9.
Yield: 38% over 4 steps [TLC: $R_f$=0.4 ⁷⁾][ESI-MS: m/e=586 (M+H)⁺].

I.3.15

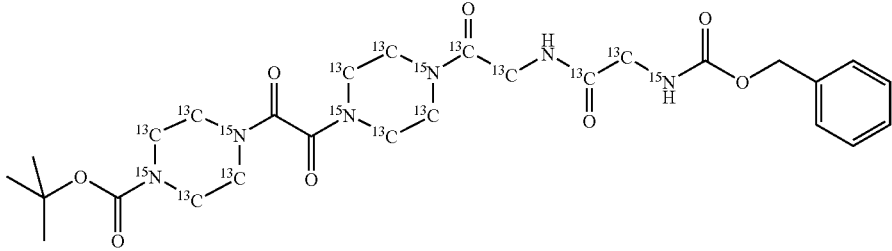

The preparation was effected in analogy with Example
I.3.7 using the building blocks:
Compound from Example SC.2.8
Oxalyl chloride
Compound from Example SC.2.7
Compound from Example SC.2.9.
Yield: 41% over 4 steps [TLC: $R_f$=0.55 [4)]. [ESI-MS: m/e=592 (M+H)$^+$].

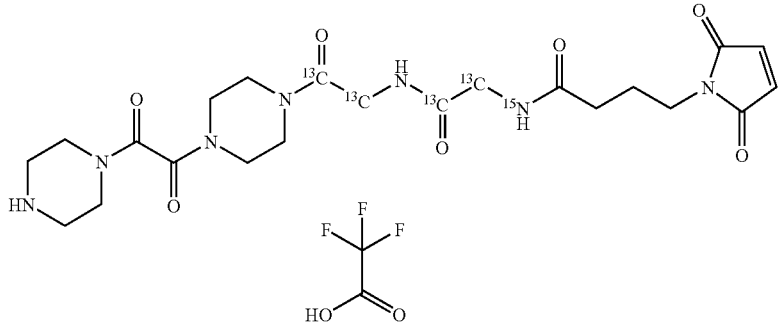

I.3.16

The preparation was effected in analogy with Examples
I.3.9 and I.3.10, proceeding from:
compound from Example I.3.13
Yield: 60% over 3 steps [TLC: $R_f$=0.16 [5)]]

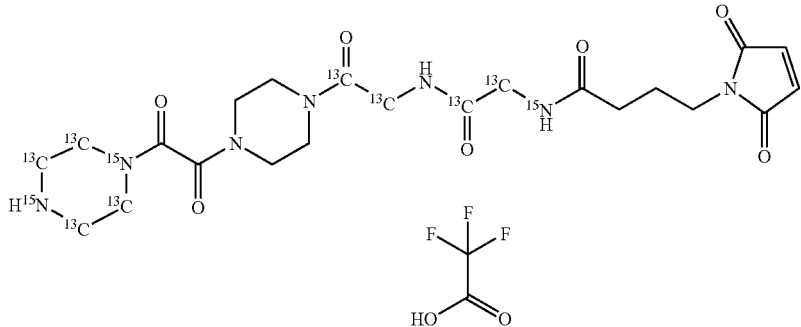

I.3.17

The preparation was effected in analogy with Examples
I.3.9 and I.3.10, proceeding from:
compound from Example I.3.14
Yield: 66% over 3 steps [TLC: $R_f$=0.16 [5)]].

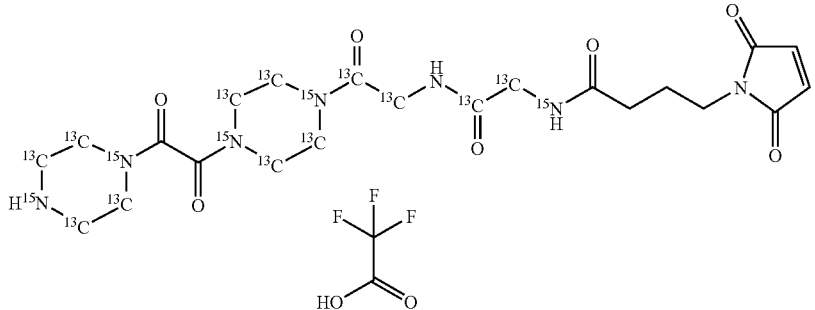

I.3.18

The preparation was effected in analogy with Examples I.3.9 and I.3.10, proceeding from:
compound from Example I.3.15
Yield: 49% over 3 steps [TLC: $R_f$=0.16 [5)]]

EXAMPLES OF ACID-CLEAVABLE AFFINITY TAGS

Example 1

Preparation Process (Variant A)

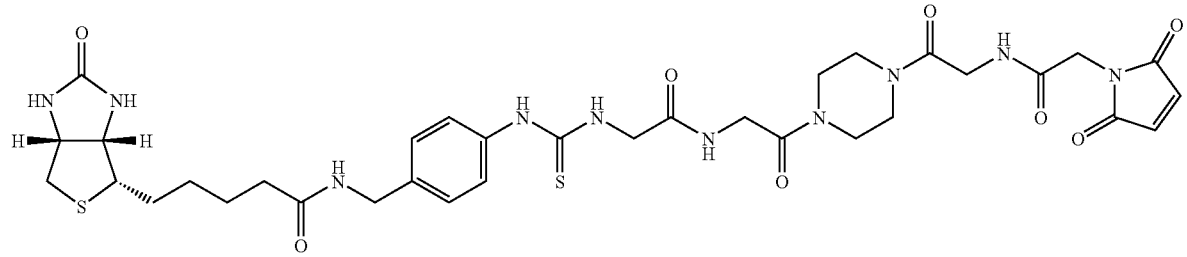

368 mg (0.63 mmol) of the intermediate I.2.1 were taken up in 5 ml of DMF, after which 500 µl of piperidine were added. After the mixture had been stirred at room temperature for 15 min, it was concentrated and the residue was purified by flash chromatography on silica gel (eluent: dichloromethane/methanol/aqueous ammonia (17%) 15/3/0.3). The appropriate fractions were combined, the solvent was evaporated in vacuo and the residue was dried. 204 mg (90%) of the target product were obtained [TLC: dichloromethane/methanol/17% ammonia 15/4/0.5 $R_f$=0.28].

26 mg (73 µmol) of this intermediate were taken up in 10 ml of DMF, after which 18.4 mg (73 µmol) of maleimidoacetic acid-N-hydroxysuccinimide ester and 19 mg of ethyldiisopropylamine were added and the mixture was stirred at RT for 1 h. Alternatively, it is also possible to couple maleimidoacetic acid to the amine component in the presence of EDCI/HOBT. The solvent was evaporated and the residue was purified by flash chromatography on silica gel (eluent [2)]). The appropriate fractions were combined, the solvent was evaporated in vacuo and the residue was dried. 34 mg (95%) of the desired product were obtained [TLC: $R_f$=0.17 [2)]].

33 mg (67 µmol) of this intermediate were taken up in 5 ml of dichloromethane, after which 1 ml of TFA was added. After the mixture had been stirred at room temperature for 15 min, it was concentrated and the residue was precipitated with diethyl ether from dichloromethane. After filtration and drying, 33 mg (97%) of the desired product were obtained as the trifluoroacetic acid salt [TLC: acetonitrile/water/glacial acetic acid 10/3/1.5 $R_f$=0.22] [ESI-MS: m/e=395 (M+H)$^+$].

32 mg (63 µmol) of the deprotected intermediate and 26 mg (70 µmol) of the isothiocyanate SC.1.1 from the starting compound series 1 were dissolved in 5 ml of DMF after which 37 µl of ethyldiisopropylamine were added and the mixture was then stirred at RT for 4 h. The mixture was concentrated and the residue was stirred up with water and filtered off with suction. The residue was separated off and then treated three times with dichloromethane/methanol 1:1, and a further twice with methanol, in an ultrasonic bath. After drying, 19 mg (35%) of the target compound were obtained [TLC: $R_f$=0.5 [5)]] [ESI-MS: m/e=785 (M+H)$^+$].

Example 2

Preparation Process (Variant B)

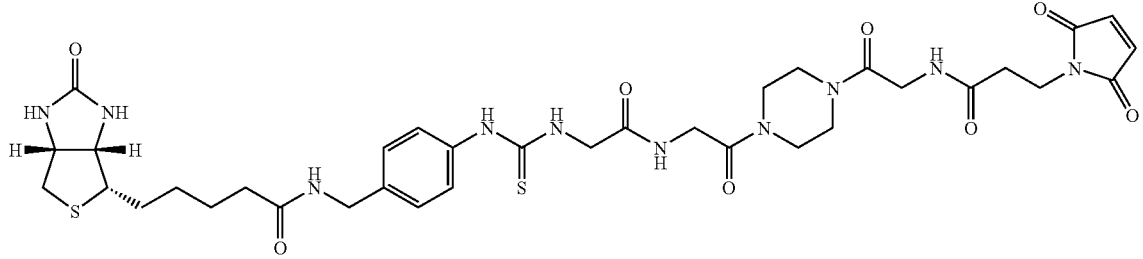

182 mg (0.31 mmol) of the compound I.1.1 were taken up in 15 ml of dichloromethane after which 1 ml of TFA was added. After the mixture had been stirred at room temperature for 15 min, it was concentrated and the residue was precipitated with diethyl ether from dichloromethane. After filtration and drying, 175 mg (94%) of the desired product were obtained as the trifluoroacetic acid salt [TLC: $R_f$=0.2 [5)]].

170 mg (286 µmol) of the deprotected intermediate were initially introduced in 10 ml of DMF, after which 112 mg (286 µmol) of the isothiocyanate SC.1.1 from the starting compound series 1 and 150 µl of ethyldiisopropylamine were added and the mixture was then stirred overnight at RT.

The mixture was concentrated and the residue was stirred up with 10 ml of water and filtered off with suction. The residue was separated off and then stirred up with dichloromethane. After filtration and drying, 244 mg (98%) of the desired compound were obtained [TLC: $R_f$=0.23 [4)]].

240 mg (0.276 mmol) of this intermediate were taken up in 10 ml of DMF after which 500 µl of piperazine were added. After the mixture had been stirred at room temperature for 30 min, it was concentrated and the residue was digested with dichloromethane. It was then filtered off and the filter residue was suspended in a mixture of 5 ml of DMF and 10 ml of dichloromethane. After 10 ml of diethyl ether had been added, the product precipitated out completely and was filtered off and dried. 135 mg (76%) of the target product were obtained [TLC: acetonitrile/water/glacial acetic acid 10/3/1.5 $R_f$=0.2].

30 mg (46 µmol) of this intermediate and 18 mg of ethyldiisopropylamine were added to a solution of 8 mg (46 µmol) of maleimidopropionic acid, 9.4 mg (70 µmol) of HOBT and 11 mg (56 µmol) of EDCI in 10 ml of DMF, which solution had previously reacted for 30 min, and the whole was then stirred overnight at RT. The solvent was evaporated off and the residue was stirred up with 5 ml of water. The solid residue was then stirred up with 5 ml of dichloromethane/methanol 1:1, after which 5 ml of diethyl ether were added. The precipitated product was dried under high vacuum. 28 mg (76%) were obtained [TLC: $R_f$=0.4 [5)]] [ESI-MS: m/e=799 (M+H)$^+$].

The following examples were prepared in an analogous manner to Example 1 (Variant A) or Example 2 (Variant B). The variant is indicated below in each case.

Example 3

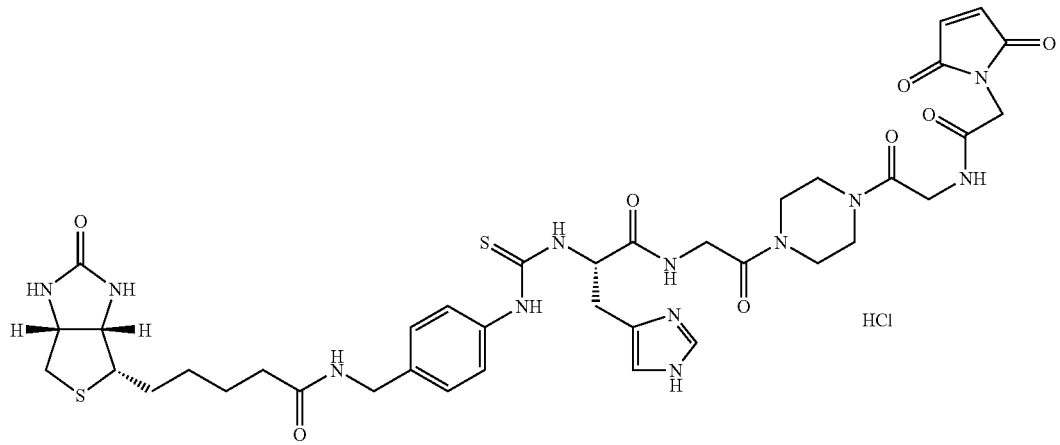

Starting compounds: I.2.2, SC. 1.1; Variant A
Yield: 33% over 4 steps, then conversion into the hydrochloride using 1.5 equivalents of a 0.1 M aqueous solution of hydrochloric acid $R_f$=0.3 [6)] [ESI-MS: m/e=865 (M+H)$^+$]

Example 4

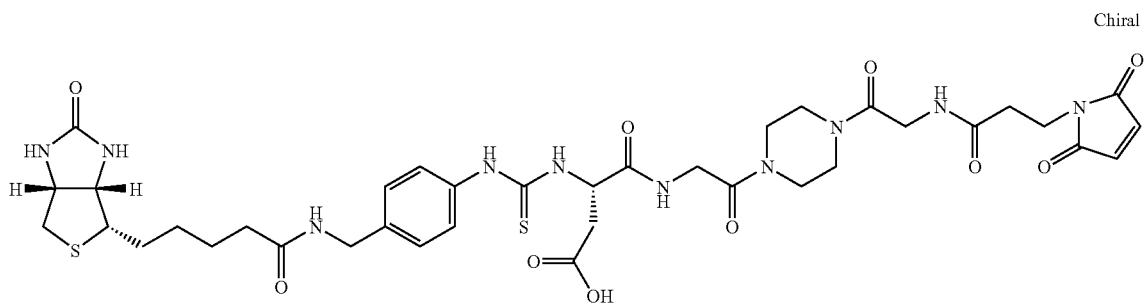

Starting compounds: I.2.3, SC.1.1; Variant A
Special features: EDCI/HOBT was used to attach maleimidopropionic acid instead of maleimidoacetic acid N-hydroxysuccinimide ester
Yield: 33% over 4 steps $R_f$=0.33 [5)] [ESI-MS: m/e=857 (M+H)$^+$]

Example 5

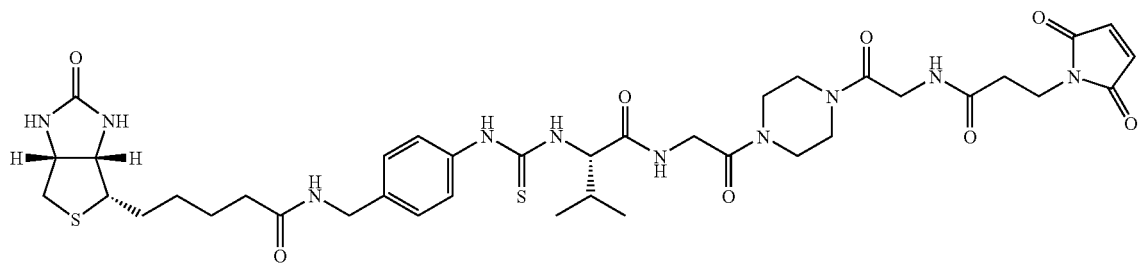

Starting compounds: I.2.4, SC.1.1; Variant A
Special features: EDCI/HOBT was used to attach maleimidopropionic acid instead of maleimidoacetic acid N-hydroxysuccinimide ester
Yield: 30% over 4 steps $R_f$=0.55 [5)] [ESI-MS: m/e=841 (M+H)+]

Example 6

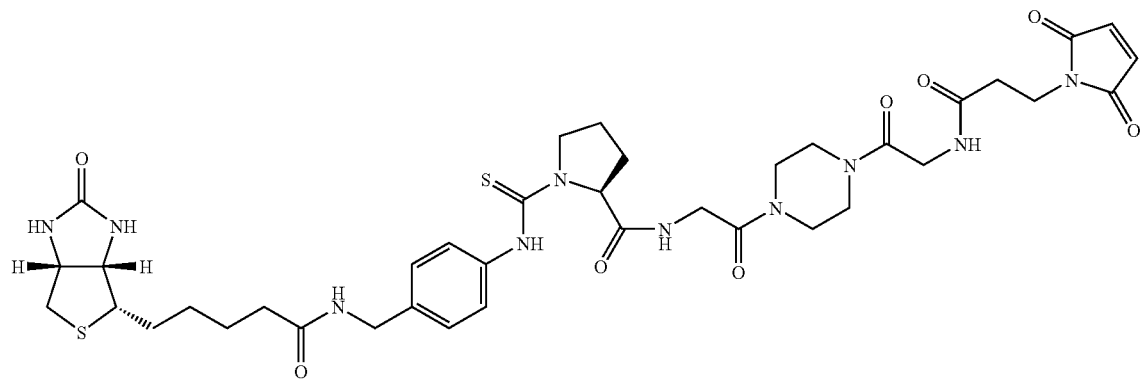

Starting compounds: I.2.6, SC.1.1; Variant A
Special features: EDCI/HOBT was used to attach maleimidopropionic acid instead of maleimidoacetic acid N-hydroxysuccinimide ester
Yield: 23% over 4 steps $R_f$=0.44 [5)] [MALDI-MS: m/e=861 (M+Na)+]

Example 7

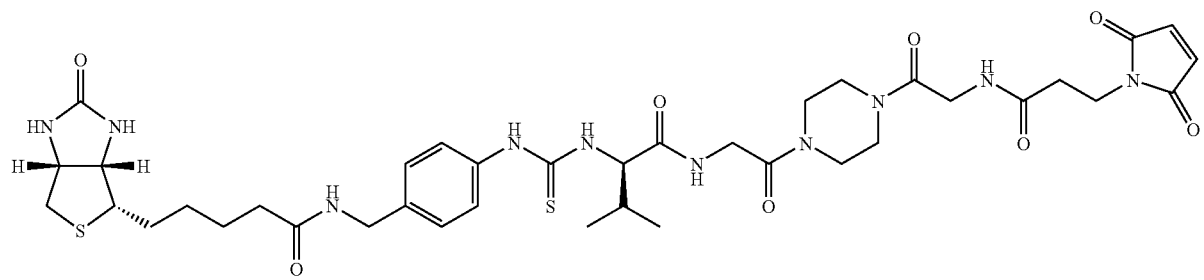

Starting compounds: I.2.7, SC.1.1; Variant A
Special features: EDCI/HOBT was used to attach maleimidopropionic acid instead of maleimidoacetic acid N-hydroxysuccinimide ester
Yield: 37% over 4 steps $R_f$=0.56 [5)] [ESI-MS: m/e=841 (M+H)+]

Example 8
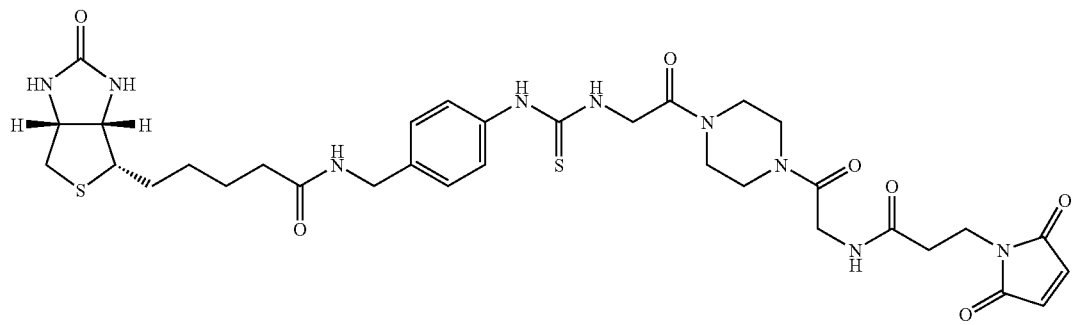
Starting compounds: I.1.1, SC.1.1; Variant A
Yield: 70% over 4 steps $R_f$=0.53 [5] [ESI-MS: m/e=742 (M+H)+]
Example 9
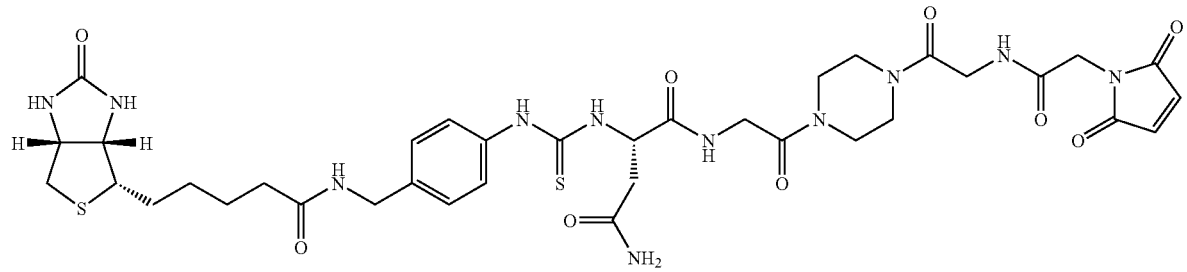
Starting compounds: I.2.5, SC.1.1; Variant B
Yield: 57% over 4 steps $R_f$=0.28 [5] [MALDI-MS: m/e 878 (M+Na)+]
Example 10
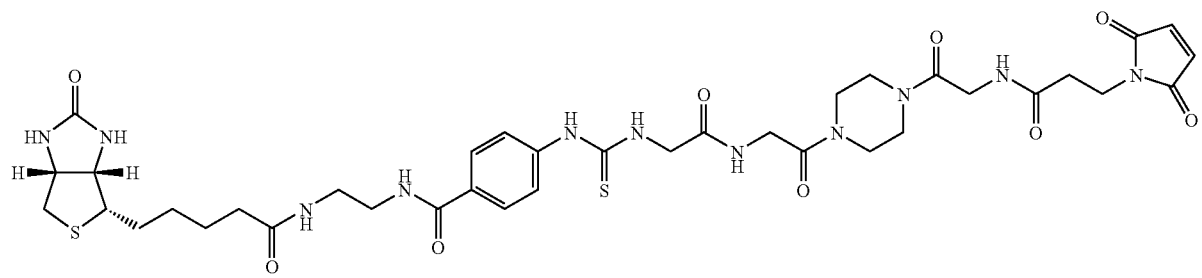
Starting compounds: I.2.1, SC.1.3; Variant A
Yield: 34% over 4 steps $R_f$=0.25 [5] [MALDI-MS: m/e=878 (M+Na)+]

Example 11

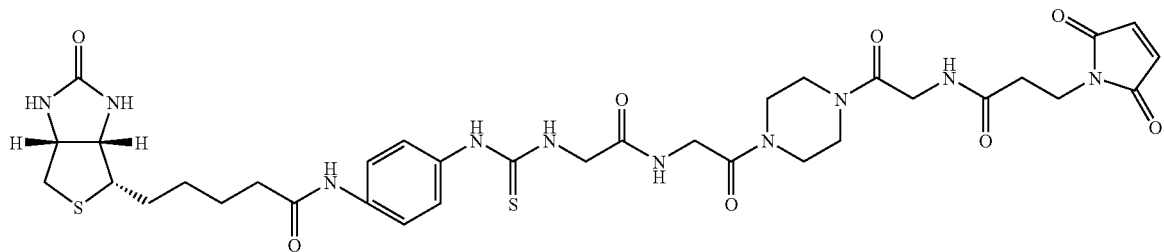

Starting compounds: I.2.1, SC.1.2; Variant A
Yield: 31% over 4 steps $R_f$=0.4 [5] [MALDI-MS: m/e 807 (M+Na)$^+$]

Example 12

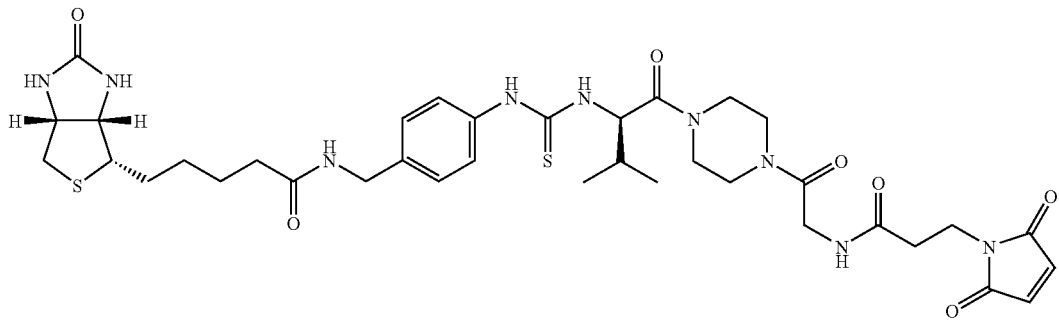

Starting compounds: I.1.2, SC.1.1; Variant A
Yield: 34% over 4 steps $R_f$=0.38 [4] [ESI-MS: m/e=784 (M+H)$^+$]

Example 13

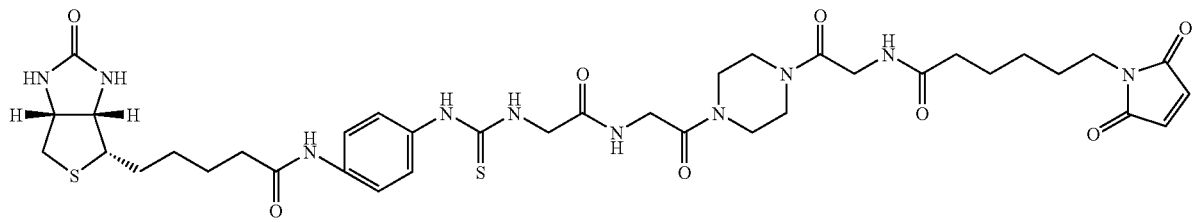

Starting compounds: I.2.1, SC.1.2; Variant B
Special features: Instead of attaching maleimidopropionic acid in the presence of EDCI/HOBT, the amine precursor of the end product was, in this present case, reacted, in the last step, with ε-maleimidocaprylic acid in the presence of EDCI/HOBT.
Yield: 15 mg (19% over 4 steps) $R_f$=0.5 [5] [ESI-MS: m/e=827 (M+H)$^+$]

Example 14

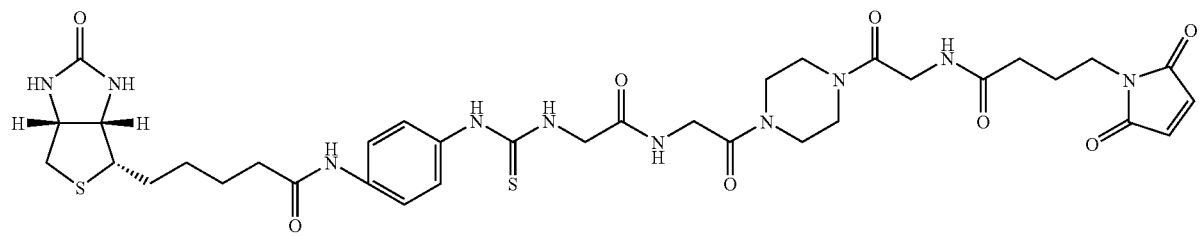

Starting compounds: I.2.1, SC.1.2; Variant B
Special features: Instead of attaching maleimidopropionic acid in the presence of EDCI/HOBT, the amine precursor of the end product was, in this present case, reacted, in the last step, with ε-maleimidobutyric acid in the presence of EDCI/HOBT.

Yield: 12% over 4 steps $R_f$=0.5 [5)] [ESI-MS: m/e=799 (M+H)$^+$]

Example 15

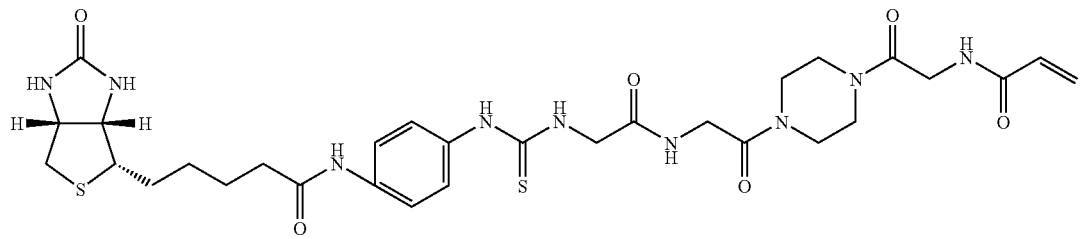

Starting compounds: I.2.1, SC.1.2; Variant B
Special features: Instead of attaching maleimidopropionic acid in the presence of EDCI/HOBT, the amine precursor of the end product was, in this present case, reacted, in the last step, with acryloyl chloride (6 equiv.) in dichloromethane in the presence of 2 equivalents of pyridine. The resulting target compound was purified by flash chromatography (eluent: acetonitrile/water 10/1).

Yield: 3% over 4 steps $R_f$=0.15 [4)] [ESI-MS: m/e=688 (M+H)$^+$]

Example 16

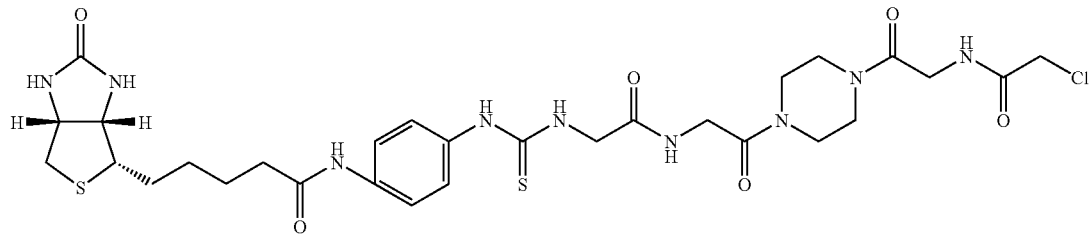

Starting compounds: I.2.1, SC.1.2; Variant B
Special features: Instead of attaching maleimidopropionic acid in the presence of EDCI/HOBT, the amine precursor of the end product was, in this present case, reacted, in the last step, with chloroacetyl chloride in dichloromethane in the presence of 2 equivalents of pyridine.

Yield: 22% over 4 steps $R_f$=0.12 [1)] [MALDI-MS: m/e=732 (M+Na)$^+$]

Example 17
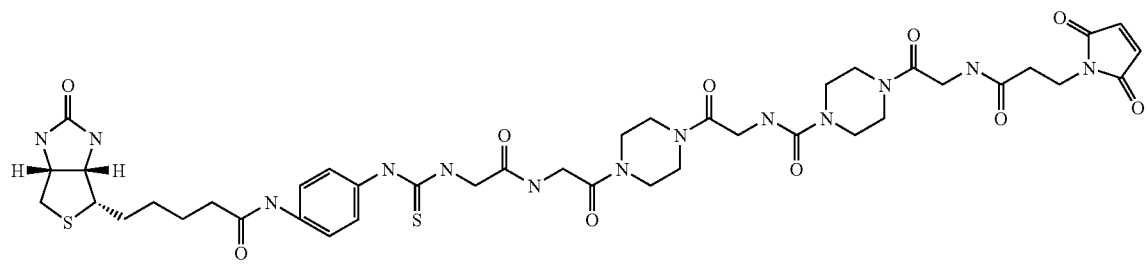
Starting compounds: I.3.4, SC.1.2; Variant B
Yield: 58% over 4 steps $R_f$=0.2 [5)] [ESI-MS: m/e=954 (M+H)+]
Example 18
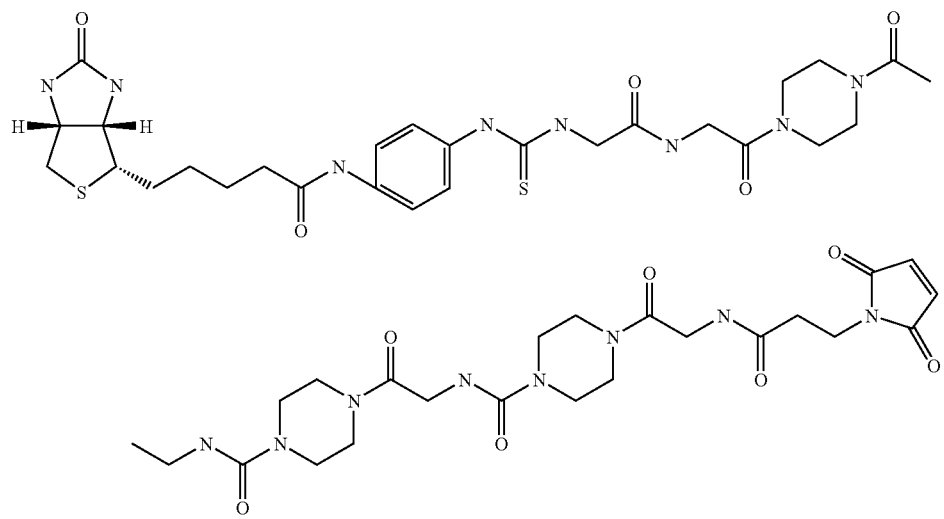
Starting compounds: I.3.5, SC.1.2; Variant B
Example 19
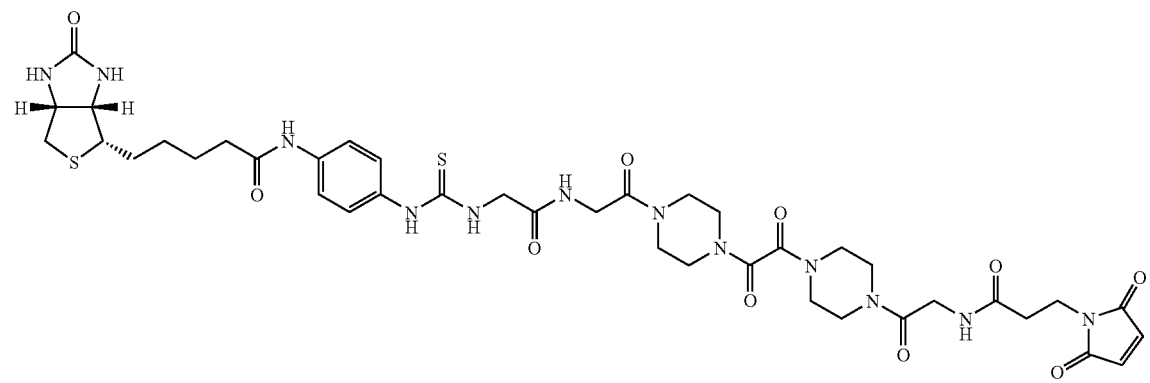
Starting compounds: I.3.1, SC.1.2; Variant B
Yield: 83% over 4 steps $R_f$=0.4[5)] [ESI-MS: m/e=925 (M+H)+]

Example 20
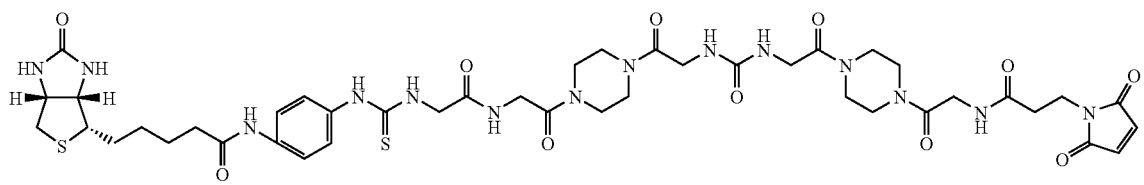
Starting compounds: I.3.3, SC.1.2; Variant B
Example 21
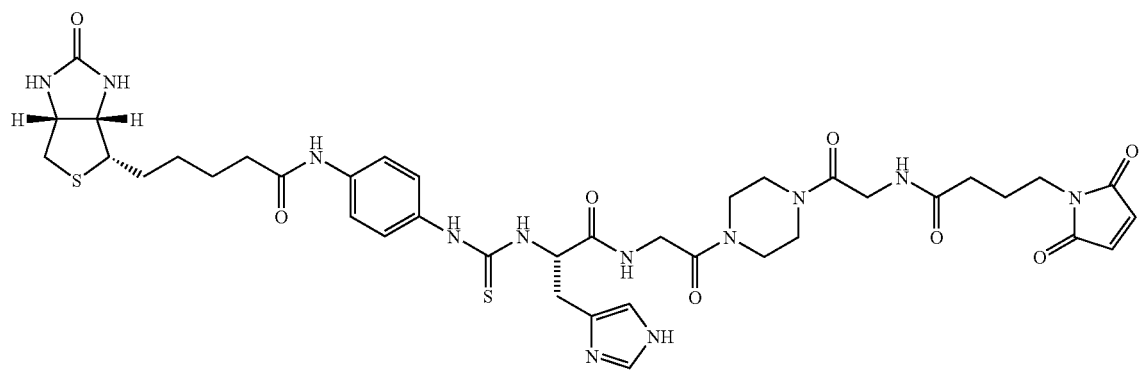
Starting compounds: I.2.2, SC.1.2; Variant B
Yield: 56% over 4 steps $R_f$=0.3 [8)] [ESI-MS: m/e=879 (M+H)+]
Example 22
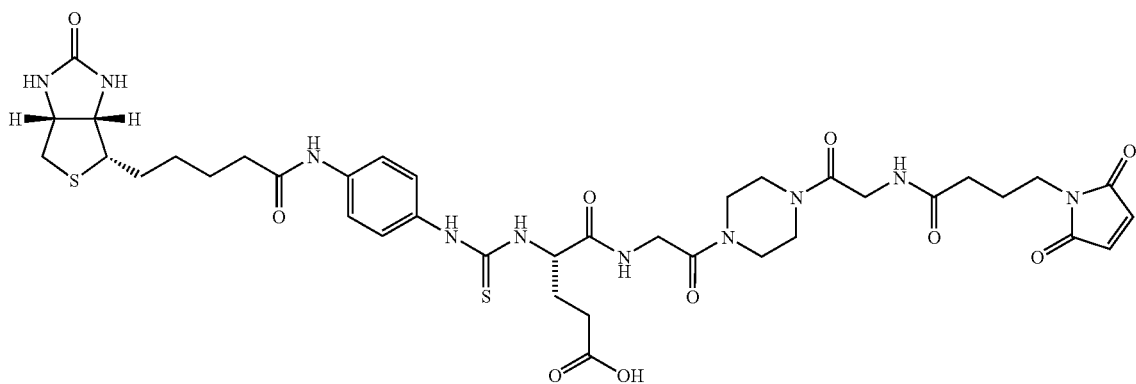
Starting compounds: I.2.9, SC.1.2; Variant A
Yield: 26% over 4 steps $R_f$=0.5 [5)] [ESI-MS: m/e=871 (M+H)+]

Example 23

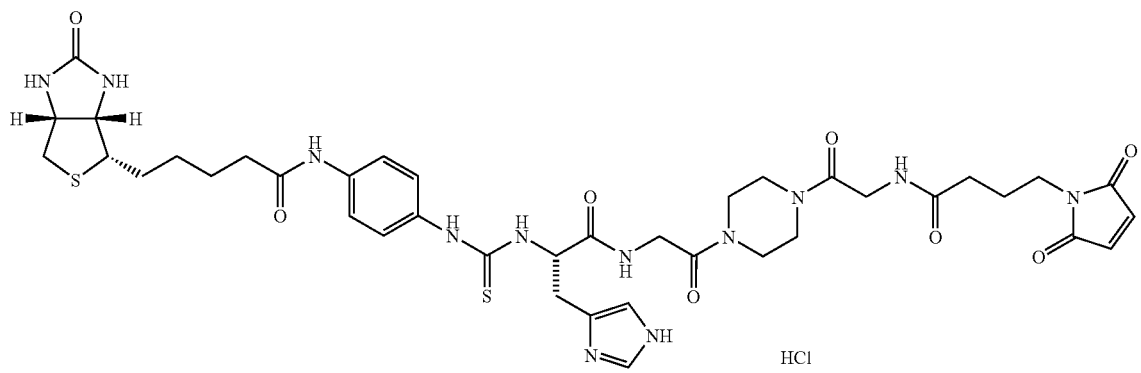

The preparation was effected by converting the compound from Example 21 into the hydrochloride using 0.1 M aqueous HCl $R_f$=0.23 [6)] [ESI-MS: m/e=879 (M+H)+]

Example 24

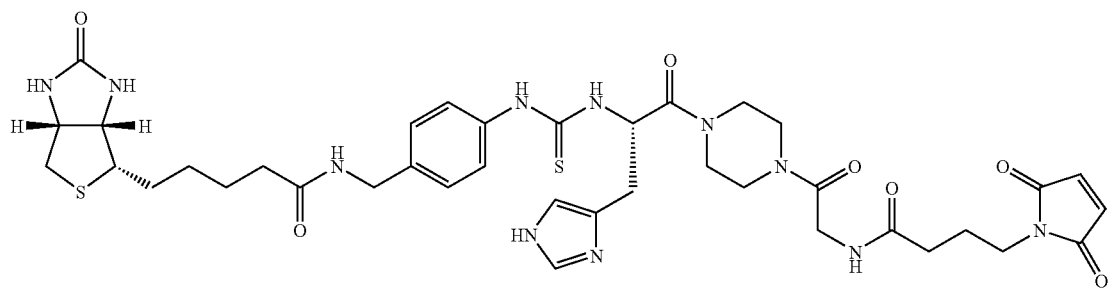

Starting compounds: I.1.1, SC.1.1; Variant B
Yield: 47% over 4 steps $R_f$=0.5 [5)] [ESI-MS: m/e 756 (M+H)+]

Example 25

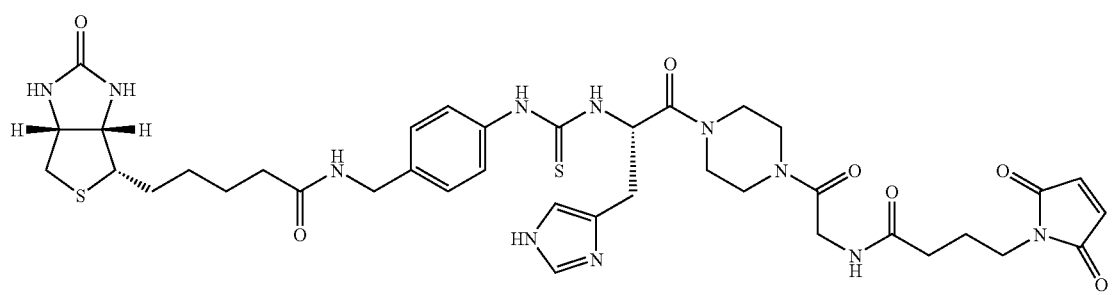

Starting compound: SC.2.3, after which there then came the following standard reactions:
Linkage to ω-maleimidobutyric acid in the presence of EDCI/HOBT (61%), Boc elimination (88%),
Linkage to bis-Boc-histidine N-hydroxysuccinimide ester (52%), Boc elimination (69%),
Reaction with SC.1.1 (96%).
$R_f$=0.4 [6)] [ESI-MS: m/e=836 (M+H)+]

Example 26

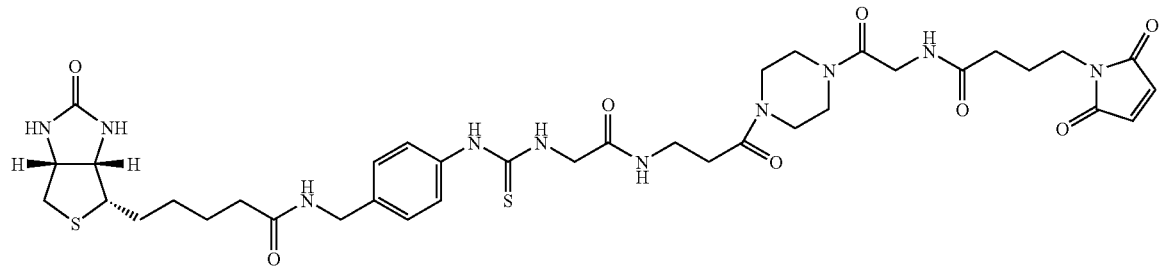

Starting compounds: I.2.8, SC.1.1; Variant B
Yield: 23% over 4 steps $R_f$=0.3 [5)] [ESI-MS: m/e=827 (M+H)+]

Example 27

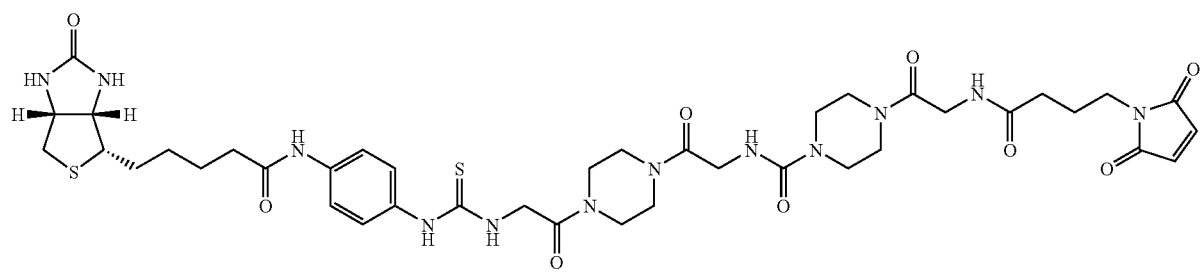

Starting compounds: I.3.6, SC.1.2; Variant B
Yield: 27% over 4 steps $R_f$=0.26 [5)] [ESI-MS: m/e=911 (M+H)+]

Example 28

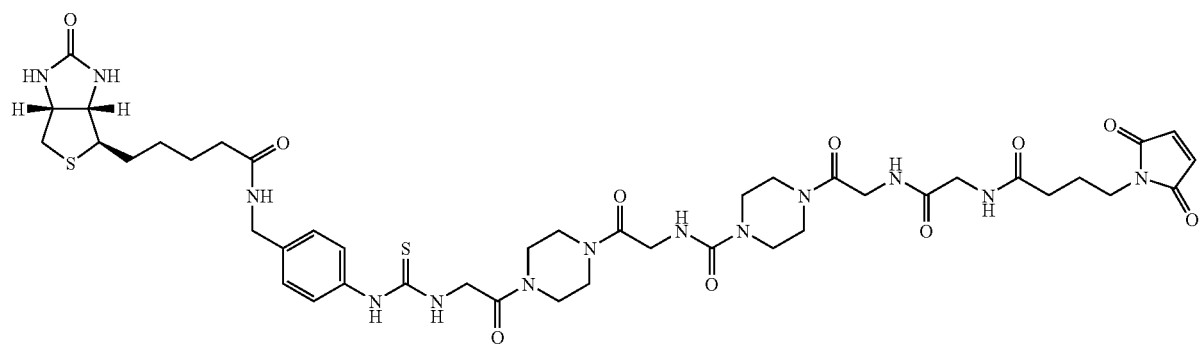

Starting compound: I.3.10, after which there then came the following standard reactions:
Linkage to Boc-glycine N-carboxylic acid anhydride (71%),
Boc elimination using trifluoroacetic acid (80%)
Linkage to SC.1.1 (54%).
$R_f$=0.38 [5)] [ESI-MS: m/e=953 (M+H)+]

Example 29

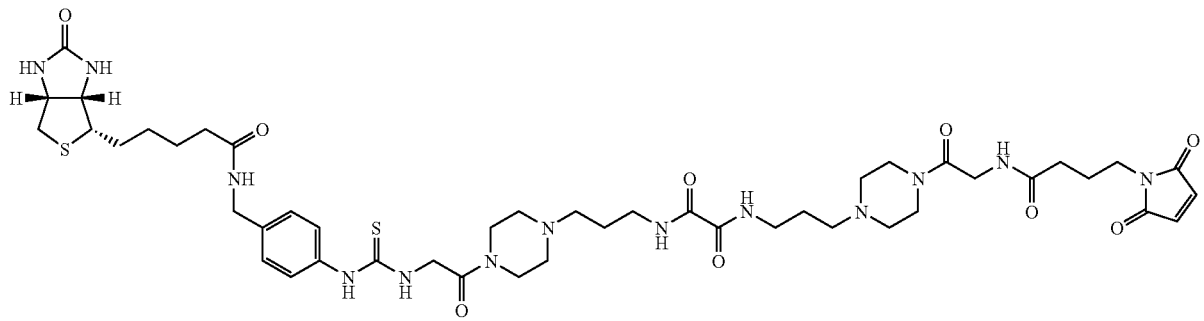

Starting compound: I.3.8, after which there then came the following standard reactions:

Boc elimination at both terminal amino groups using trifluoroacetic acid (quant.), reaction with ½ equiv. of the compound SC.1.1 to give the monothiourea (28%) [$R_f$= 0.15 [9)]]

Reaction with ω-maleidobutyric acid in the presence of EDCI/HOBT (50%) [ESI-MS: m/e=1010 (M+H)+]

Example 30

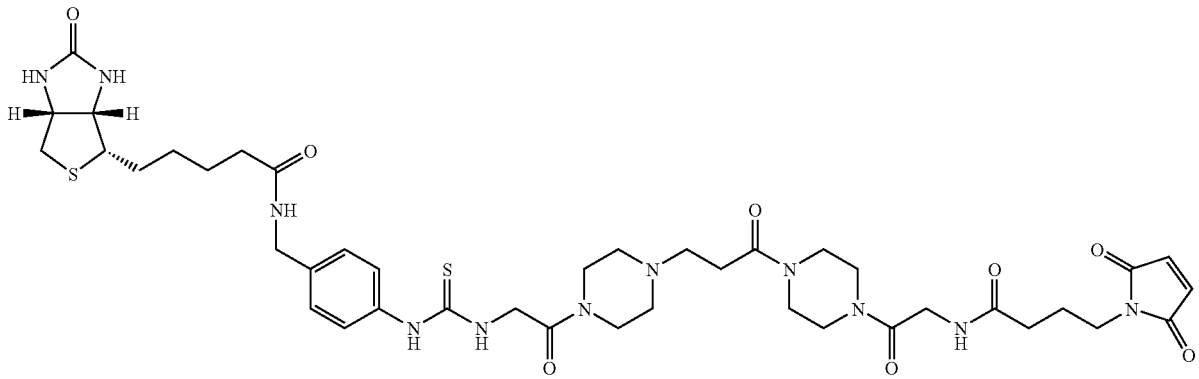

Starting compound: I.3.12, after which there then came the following standard reactions:

Reaction with Boc-glycine N-carboxylic acid anhydride (84%),

Boc elimination using trifluoroacetic acid (quant.), [$R_f$=0.28 [8)]]

Reaction with SC.1.1 (60%), [$R_f$=0.46 [6)]][ESI-MS: m/e=896 (M+H)+]

Example 31

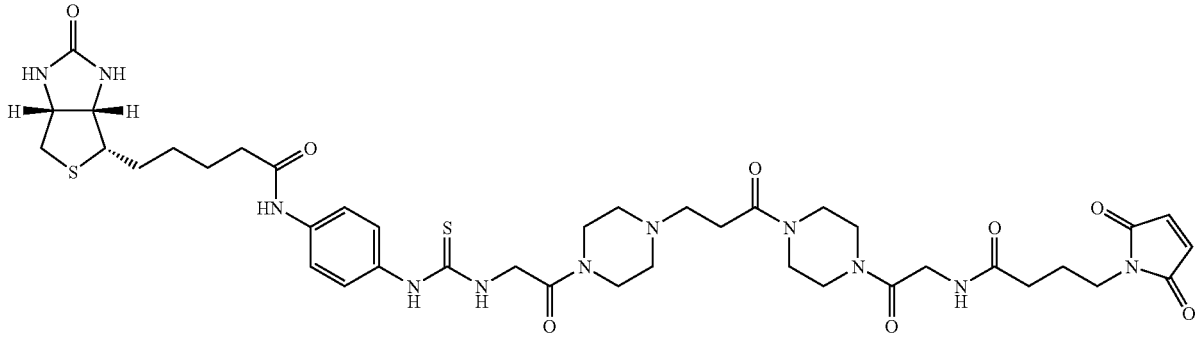

The preparation was effected in analogy with the compound from Example 30.

Reaction with SC.1.2 instead of SC.1.1 (52%), [$R_f$= 0.55 [6)]][ESI-MS: m/e=882, (M+H)+]

Example 32

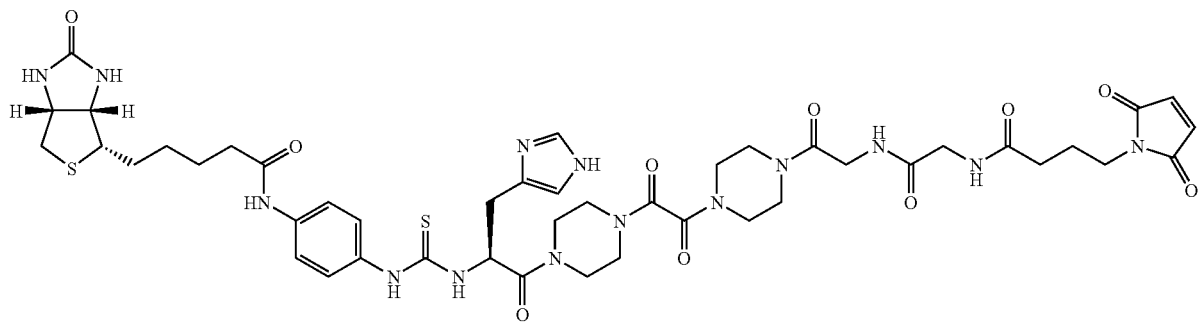

Starting compound: I.3.10, after which there then came the following standard reactions:
Reaction with bis-Boc-histidine H-hydroxysuccinimide ester (39%)
Boc elimination using trifluoroacetic acid (87%), [$R_f$=0.44 [8)]]
Reaction with SC.1.2 (45%), [$R_f$=0.44 [6)]][ESI-MS: m/e=1019 (M+H)$^+$]

Example 33

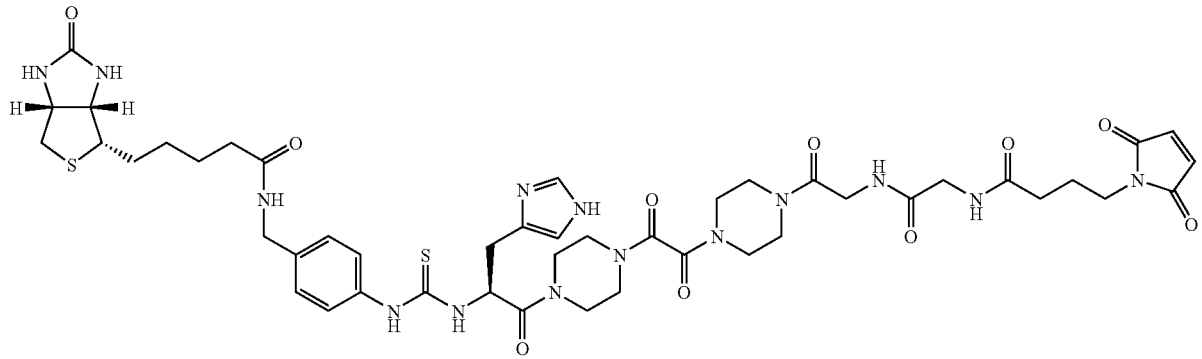

The preparation was effected in analogy with the compound from Example 32.
Reaction with SC.1.1 instead of SC.1.2 (35%), [$R_f$=0.3 [6)]][ESI-MS: m/e=1033 (M+H)$^+$]

Example 34

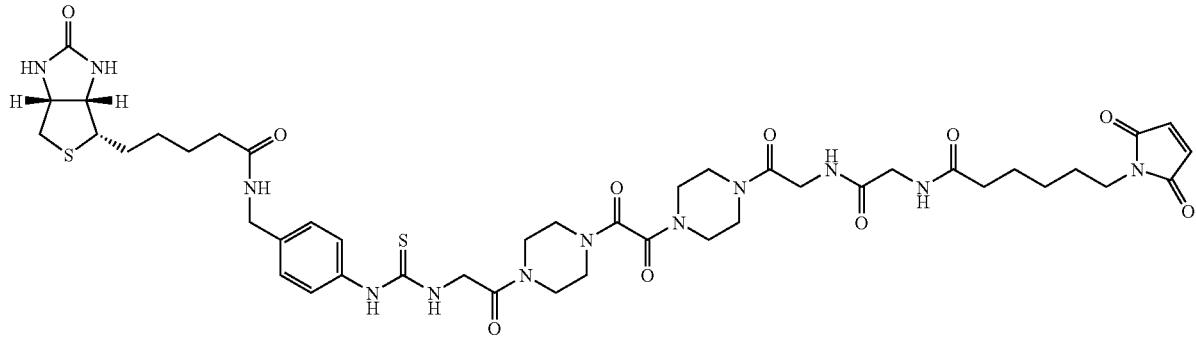

Starting compound: I.3.11, after which there then came the following standard reactions:
Reaction with Boc-glycine N-carboxylic acid anhydride (69%)

Boc elimination using trifluoroacetic acid (quant.), [$R_f$=0.3 [6)]]
Reaction with SC.1.1 (97%), [$R_f$=0.44 [6)]][ESI-MS: m/e=981 (M+H)$^+$]

Example 35

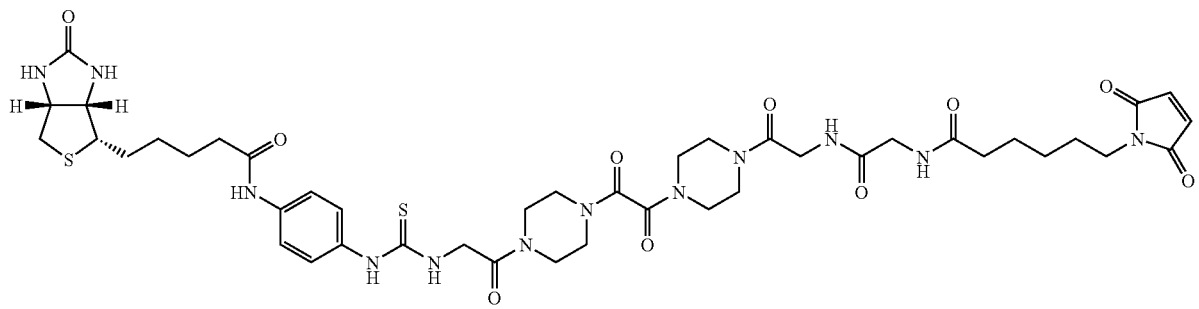

The preparation was effected in analogy with the compound from Example 34

Reaction with SC.1.2 instead of SC.1.1 (73%), [$R_f$= 0.48 [5)]][ESI-MS: m/e=967 (M+H)+]

Example 36

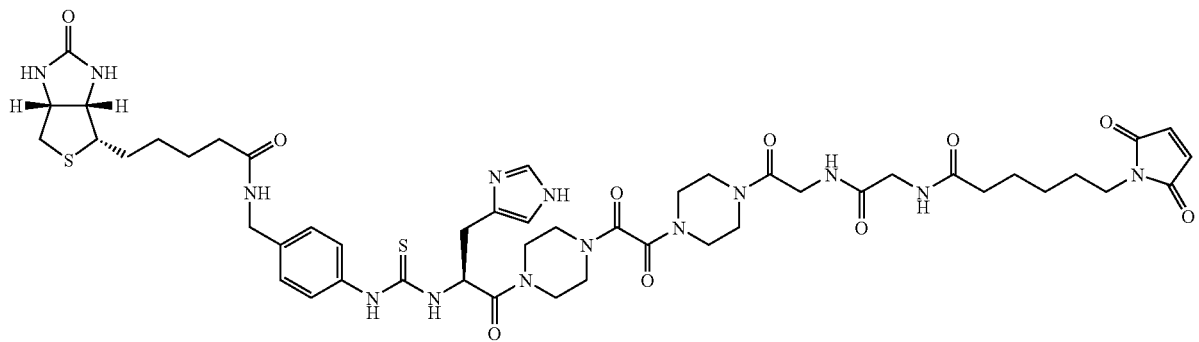

Starting compound: I.3.11, after which there then came the following standard reactions:

Reaction with bis-Boc-histidine N-hydroxysuccinimide ester (41%)

Boc elimination using trifluoroacetic acid (quant.), [$R_f$=0.12 [6)]]

Reaction with SC.1.1 (90%), [$R_f$=0.38 [6)]][ESI-MS: m/e 1061 (M+H)+]

Example 37

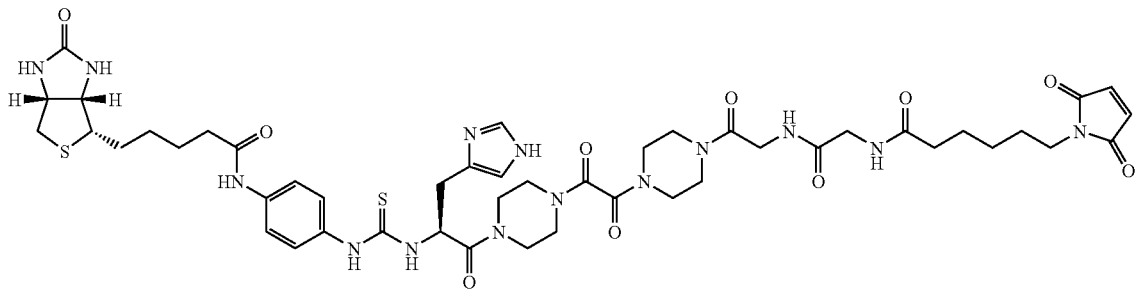

The preparation was effected in analogy with the compound from Example 36.

Reaction with SC.1.2 instead of SC.1.1 (73%), [$R_f$= 0.4 [6)]][ESI-MS: m/e=1047 (M+H)+]

Example 38

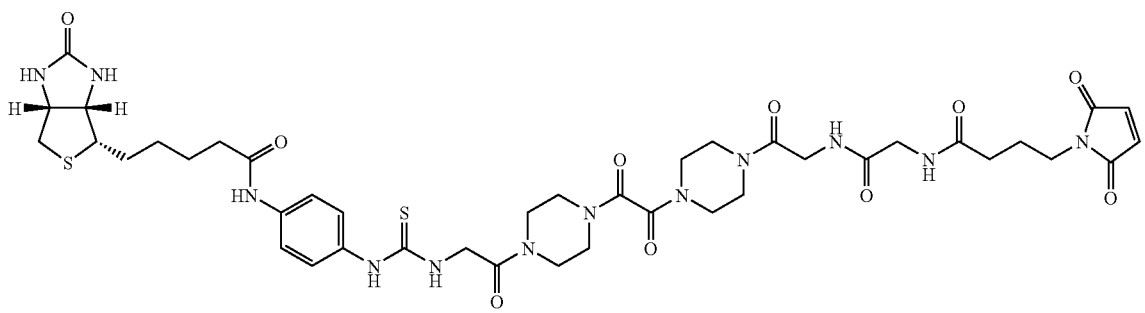

The preparation was effected in analogy with the compound from Example 28.

Reaction with SC.1.2 instead of SC.1.1 (72%), [$R_f$= 0.45 [5)][ESI-MS: m/e=(M+H)$^+$]

Together with the affinity tags from Examples 39, 40 and 41, this affinity tag forms an affinity tag quadruplet which makes it possible to analyze four proteome samples in parallel.

Example 39

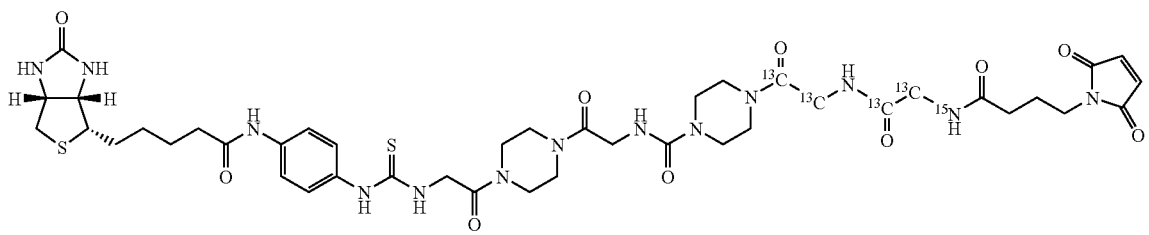

Starting compound: I.3.16, after which there then came the following standard reactions:
  Linkage to Boc-glycine N-carboxylic acid anhydride (81%),
  Boc elimination using trifluoroacetic acid (98%),
  Linkage to SC.1.2 (81%)
  $R_f$=0.5 [5)] [ESI-MS: m/e=944 (M+H)$^+$]

Example 40

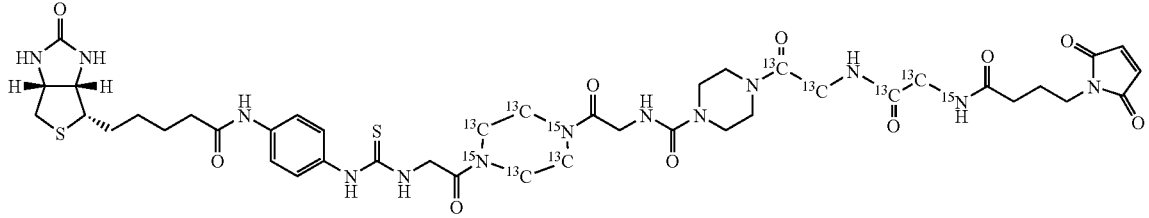

Starting compound: I.3.17, after which there then came the following standard reactions:
  Linkage to Boc-glycine N-carboxylic acid anhydride (80%),
  Boc elimination using trifluoroacetic acid (quant.),
  Linkage to SC.1.2 (74%)
  $R_f$=0.5 [5)] [ESI-MS: m/e=950 (M+H)$^+$]

Example 41

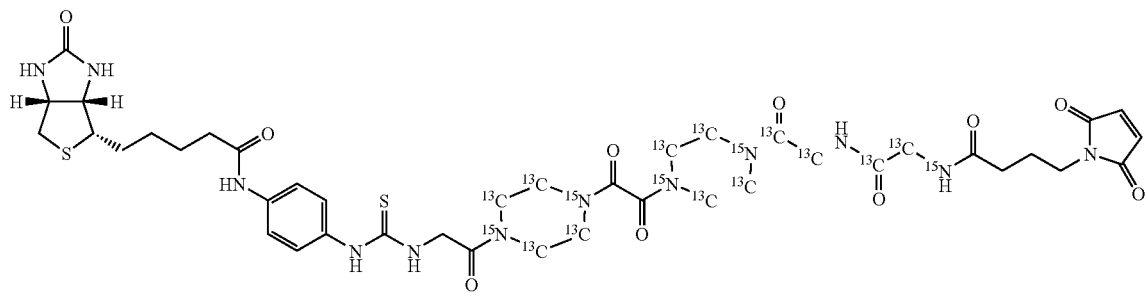

Starting compound: I.3.18, after which there then came the following standard reactions:
Linkage to Boc-glycine N-carboxylic acid anhydride (94%),
Boc elimination using trifluoroacetic acid (98%),
Linkage to SC.1.2 (38%)
$R_f$=0.5 [5)] [ESI-MS: m/e=956 (M+H)$^+$]

Example 42

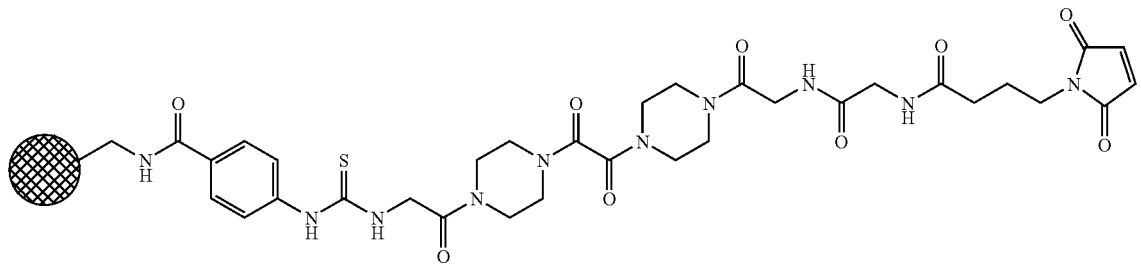

Starting compound: I.3.10, after which there then came the following standard reactions:
Linkage to Boc-glycine N-carboxylic acid anhydride (78%),
Boc elimination using trifluoroacetic acid (93%) [$R_f$= 0.2 [6)]]

In parallel with this, 100 mg (0.026 mmol) of NovaSyn TG resin 01-64-0043 were washed three times with DMF. After that, 28 mg (0.08 mmol) of 4-(Fmoc-amino)benzoic acid, 30 mg of HATU and 20 mg of diisopropylethylamine in 2 ml of DMF were added and the mixture was stirred overnight at RT. The resin was then washed four times with DMF. After that, standard conditions were used to detach the Fmoc group and the resin was washed four times with DMF. 2 ml of dioxane/water 1/1 and 10 µl of thiophosgene were added. After 1 h, 200 µl of ethyldiisopropylamine were added and, after a further 1 h, the resin was washed with water, dioxane and DMF. 35 mg of the previously prepared amine component were added in 2 ml of DMF and 25 µl of ethyldiisopropylamine. After 2 h, the resin was washed in each case twice with DMF and THF and dried.

Example 43

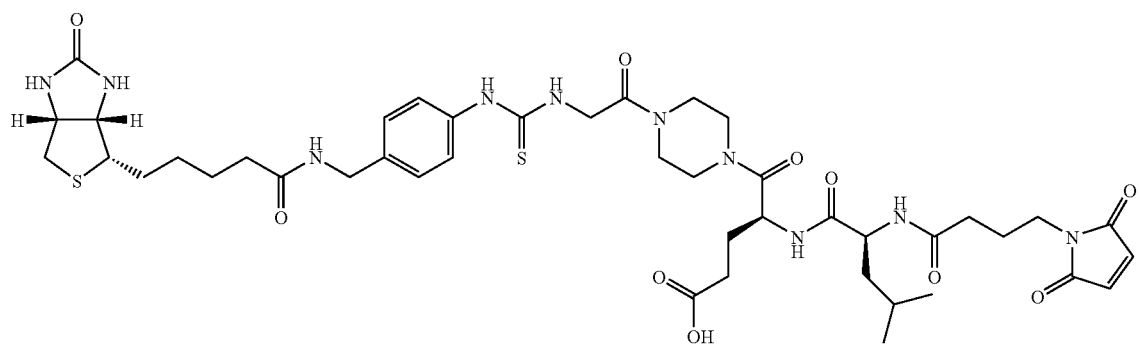

Starting compound: SC.2.10, after which there then came the following standard reactions:
Reaction with Z-Glu(tBu)-Osu (33%),
Hydrogenation over Pd—C (92%),
Reaction with Z-Leu in the presence of EDCI/HOBT (88%),
Hydrogenation over Pd—C (85%),
Linkage to ω-maleimidobutyric acid in the presence of EDCI/HOBT (66%),
Boc elimination (88%),
Reaction with SC.1.1 (88%).
$R_f=0.26$ [4)] [ESI-MS: m/e=941 (M+H)$^+$]

Example 44

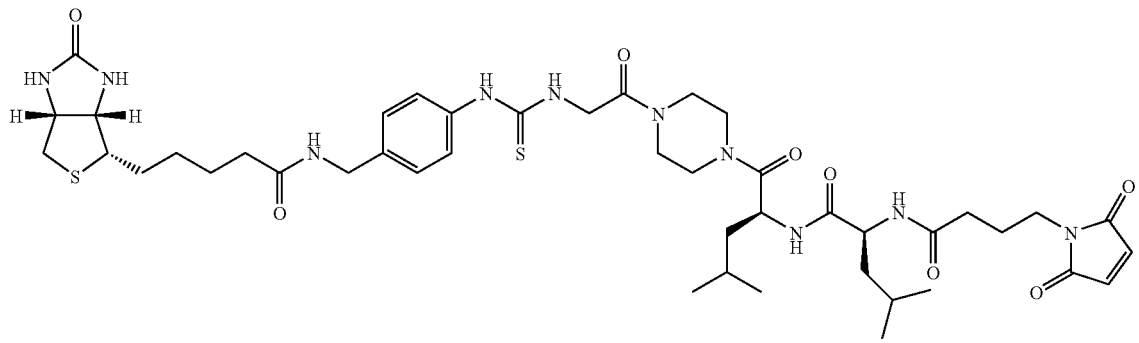

Starting compound: SC.2.10, after which there then came the following standard reactions:
Reaction with Fmoc-Leu-Leu in the presence of EDCI/HOBT (58%),
Boc elimination (78%),
Reaction with SC.1.1 (90%),
Fmoc elimination using piperidine in DMF (68%),
Linkage to ω-maleimidobutyric acid in the presence of EDCI/HOBT (72%),
$R_f=0.68$ [5)] [FAB-MS: m/e=925 (M+H)$^+$]

Example 45

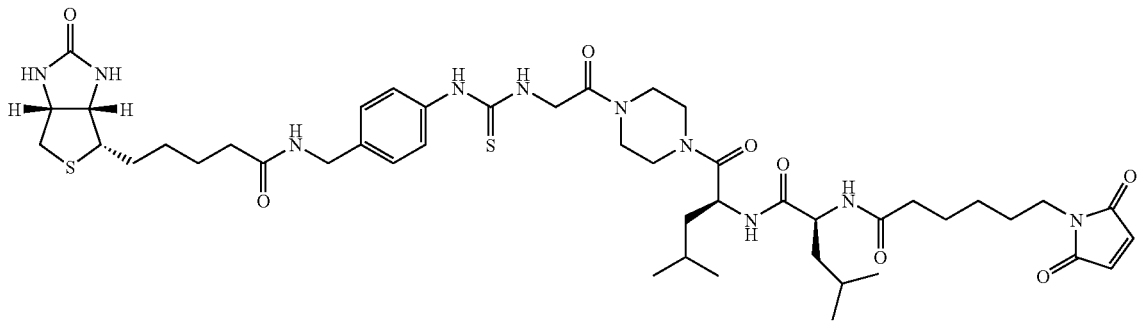

Preparation in analogy with Example 44; however, in the last step, the linkage takes place to ω-maleimidocaprylic acid in the presence of EDCI/HOBT (61%),
$R_f=0.4$ [4)] [FAB-MS: m/e=953 (M+H)$^+$]

Example 46

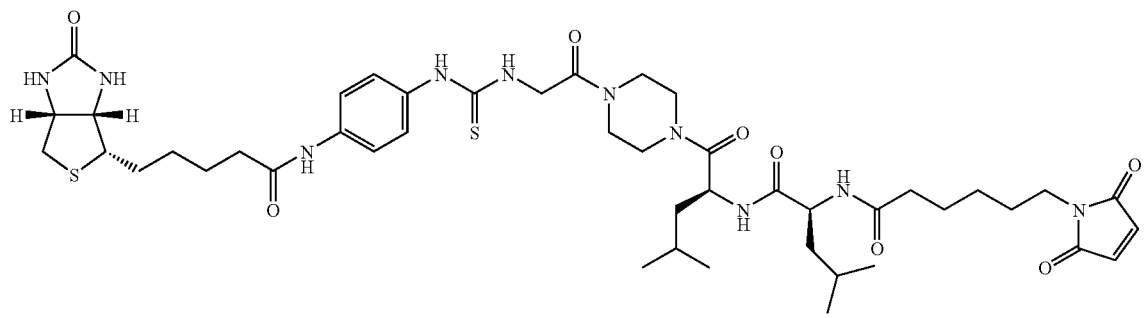

Starting compound: SC.2.10, after which there then came the following standard reactions:
Reaction with Fmoc-Leu-Leu in the presence of EDCI/HOBT (58%),
Boc elimination (78%),
Reaction with SC.1.2 (72%),
Fmoc elimination using piperidine in DMF (96%),
Linkage to ω-maleimidobutyric acid in the presence of EDCI/HOBT (92%),
$R_f$=0.4 [4)] [ESI-MS: m/e=911 (M+H)$^+$]

Example 47

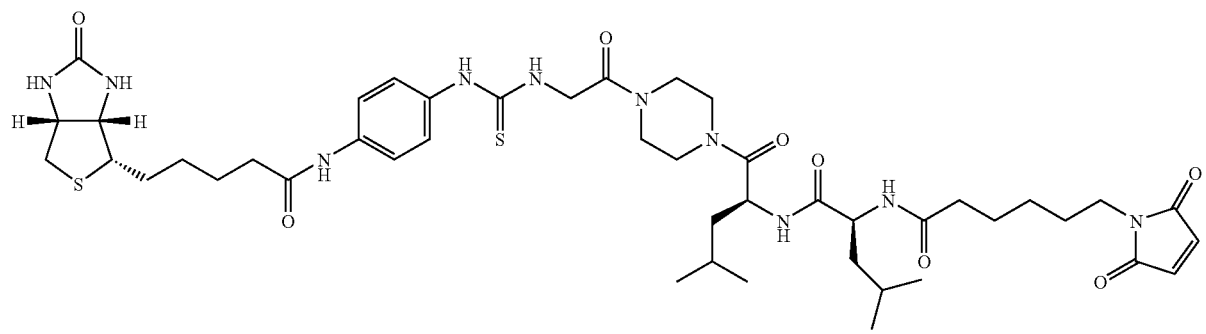

Preparation in analogy with Example 46; however, in the last step, the linkage takes place to ω-maleimidocaprylic acid in the presence of EDCI/HOBT (61%),
$R_f$=0.5 [4)] [FAB-MS: m/e=939 (M+H)$^+$]

Example 48

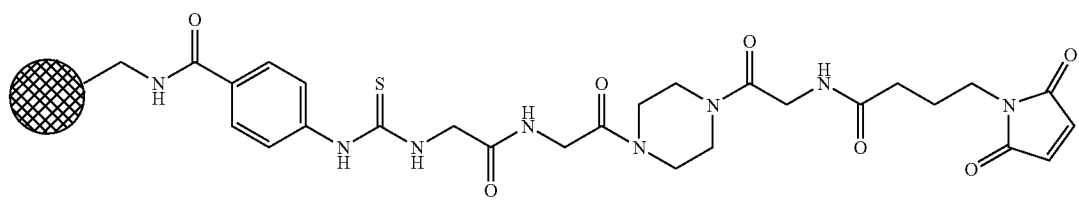

Starting compound 1.2.1, after which there then came the following standard reactions:
Boc elimination using trifluoroacetic acid (94%) [$R_f$=0.2 [5)]]. This thereby gives the amine component A.

In parallel with this, 42 mg (0.04 mmol) of aminopropyl silica gel (Aldrich, 36425-8, loading 0.95 mmol/g) were suspended in 2 ml of DMF, after which 45 mg (0.12mmol) of 4-(Fmoc-amino)phenylacetic acid, 2 µl of diisopropylethylamine, 15 mg (0.12 mmol) of diisopropylcarbodiimide and 16 mg (0.12 mmol) of HOBT were added consecutively. The mixture is allowed to stand at RT overnight, after which the resin is washed four times with DMF.

The Fmoc group is then detached using 2 ml of 20% piperidine in DMF and the resin is washed in each case four times with DMF and dioxane.

1 ml of dioxane and 45 µl of thiophosgene are then added. After 1 h, 900 µl of ethyl diisopropylamine are added and, after a further 1 h, the resin is washed in each case three times with dioxane, DMF and DCM.

47 mg (0.08 mmol) of the previously prepared amine component are added in 2 ml of DMF and 40 µl of ethyldiisopropylamine. The mixture is left to stand overnight at RT and the resin is then washed four times with DMF.

The Fmoc group is detached once again using 2 ml of 20% piperidine in DMF and the resin is washed four times with DMF.

1 ml of DMF is added, after which 22 mg (0.12 mmol) of 4-maleimidobutyric acid, 15 mg (0.12 mmol) of diisopropylcarbodiimide and 16 mg (0.12 mmol) of HOBT are added consecutively and the mixture is stirred overnight at RT. The resin is then washed in each case three times with DMF, DCM and THF.

Investigations Involving Protein Analysis

Coupling the Affinity Tags to SDS-7 and Description of the Operational Procedure for the Affinity Tag from Example 11

A mixture of seven proteins, which are also used as a size standard in gel electrophoresis (SDS-7 markers, Sigma-Aldrich GmbH, Taufkirchen) was used as the sample.

24 μg of the protein mixture were dissolved in 5 μl of buffer 1 and this solution was diluted with 135 μl of buffer 3. The proteins were denatured by heating at 100° C. for 3 minutes. In order to reduce the cysteines which were present, 3 μl of reducing solution were added and the mixture was incubated at 100° C. for 10 minutes. In order to react the free cysteines with the affinity tag from Example 11, 5 μl of derivatizing solution were then added and the mixture was incubated at 37° C. for 90 minutes.

After the derivatization, 3 μl of trypsin solution were added. The proteins are cleaved overnight (approx. 17 hours) at 37° C.

Buffer 1: 50 mM Tris-HCl, pH 8.3; 5 mM EDTA; 0.5% (w/v) SDS

Buffer 2: 10 mM NH$_4$acetate, pH 7

Buffer 3: 50 mM Tris-HCl, pH 8.3; 5 mM EDTA

Reducing solution: 50 mM TECP in buffer 2

Derivatizing solution: 30 μg of affinity tag (Example 11)/μl in DMSO

Trypsin solution: 1 mg of trypsin (Promega GmbH, Mannheim)/ml in buffer 3

Affinity Purification of Derivatized Peptides

The affinity columns (Monomeric Avidin, Perbio Science Deutschland GmbH, Bonn), having a column volume of 200 μl, were prepared freshly prior to the purification and made ready by means of the following washing steps:

two column volumes of 2×PBS
four column volumes of 30% (v/v) acetonitrile/0.4% (v/v) trifluoroacetic acid
seven column volumes of 2×PBS
four column volumes of 2 mM biotin in 2×PBS
six column volumes of 100 mM glycine, pH 2.8
six column volumes of 2×PBS Prior to loading, 30 μl of sample were diluted with 30 μl of 2×PBS, after which the diluted sample was loaded onto the column. After that, the following washing steps were carried out in order to remove the unbiotinylated peptides:

six column volumes of 2×PBS
six column volumes of PBS
six column volumes of 50 mM ammonium hydrogencarbonate/20% (v/v) methanol
one column volume of 0.3% (v/v) formic acid The sample was eluted by means of the following steps:
three column volumes of 0.3% (v/v) formic acid
three column volumes of 30% (v/v) acetonitrile/0.4% (v/v) trifluoroacetic acid The eluate was evaporated down to dryness and only dissolved once again shortly before carrying out the mass spectrometric analysis.

PBS: 10× stock solution, GibcoBRL, Cat. No. 14200-067

Mass-Spectrometric Analysis

An ion trap mass spectrometer (LCQdeka, ThermoFinnigan, San Jose) which was connected directly to a high pressure liquid chromatography appliance (LC-MS) was used for analyzing the peptides. A reversed-phase column (C$_{18}$ phase) was used as the separation column. The peptides were dissolved in eluent A (0.025% (v/v) trifluoroacetic acid) and injected. They were eluted with a gradient of eluent B (0.025% (v/v) trifluoroacetic acid/84% (v/v) acetonitrile). The eluting peptides were recognized automatically by the acquisition software in the instrument and fragmented for identification. In this way, it was possible to determine the identities of the peptides unambiguously.

FIG. 1 shows an example of a fragment spectrum of a peptide from this analysis. The observed pattern identifies the peptide unambiguously as being the peptide having the sequence FLDDDLTDDIMCVK from lactalbumin, which was a constituent of the sample. The mass of the peptide, and its fragmentation, confirm that the affinity tag was cleaved by acid in the expected manner.

In all, 19 different peptides from the sample, all of which peptides carried the expected mass of the affinity tag residue in the same manner, were identified in one analysis. No cysteine-containing peptide which was still carrying a complete affinity tag was identified.

FIG. 1: Fragment spectrum of a peptide which was derivatized with the compound from Example 11 after the peptide had been isolated using avidin, i.e. possessing an acid-cleaved affinity tag.

Coupling the Affinity Tags to Proteins and Description of the Operational Procedure for the Affinity Tags in Examples 38 to 41

A mixture of seven proteins, which are also used as size standards in gel electrophoresis (SDS-7 markers, Sigma-Aldrich GmbH, Taufkirchen), was used as the sample. The two samples to be compared contained identical quantities of the following proteins:

Bovine serum albumin
Bovine alpha-lactalbumin
Soybean trypsin inhibitor
Bovine trypsin } SDS-7
Chicken ovalbumin
Human glyceraldehyde 3-phosphate dehydrogenase
Bovine carbonic anhydrase In addition, human interleukin-4, which was not present in sample 2, was added to sample 1.

About 240 μg of protein, which were distributed approximately equally between the abovementioned 7 or, respectively, 8 proteins, were used in each sample. The SDS-7 samples were first of all dissolved in 10 ml of buffer 1 and diluted with 95 μl of buffer 3. 10 μl of interleukin-4 solution were then also added to sample 1. The samples were made up to 200 μl with buffer 3 and in each case divided in half (samples 1a and 1b and 2a and 2b, respectively).

The proteins were then denatured by heating them at 100° C. for 3 minutes. In order to reduce the cysteines which were present, 3 μl of reducing solution were added and the mixtures were incubated at 100° C. for 10 minutes. In order to react the three cysteines with the affinity tags from the examples, 5 μl of derivatizing solution were added to each sample and the mixtures were incubated at 37° C. for 120 minutes. All the 4 samples were then mixed and half of the total sample was subjected to further processing.

Sample 1a: reaction with Example 38
Sample 1b: reaction with Example 41
Sample 2a: reaction with Example 39
Sample 2b: reaction with Example 40

After the reaction had taken place, the proteins were precipitated, at −20° C. for 15 minutes, by adding four times the volume of ice-cold acetone/ethanol 1:1. The sediment was washed once with acetone/ethanol/water 4:4:2 and then dried in vacuo. The sample was dissolved in 10 µl of buffer 1 and diluted with 260 µl of buffer 3. In order to cleave the proteins, 40 µl of trypsin solution were added and the sample was incubated at 37° C. for 1 h. After that, the sample was heated briefly at 95° C. in order to inactivate the enzyme.

Buffer 1: 50 mM Tris-HCl, pH 8.3; 5 mM EDTA; 0.5% (w/v) SDS
Buffer 2: 10 mM NH$_4$acetate, pH 7
Buffer 3: 50 mM Tris-HCl, pH 8.3; 5 mM EDTA
Reducing solution: 50 mM TCEP in buffer 2
Derivatizing solution: 36 µg of affinity tag (Examples 38–41)/µl in DMSO
Trypsin solution: 1 mg of trypsin (Promega GmbH, Mannheim)/ml in buffer 3

Affinity Purification of Derivatized Peptides

In order to selectively purify the derivatized peptides from the sample, an affinity purification was carried out using an avidin column (Monomeric Avidin, Perbio Science Deutschland GmbH, Bonn) which was prepared in-house. The column was prepared and used in accordance with the manufacturer's instructions. The peptides were eluted with 0.4% trifluoroacetic acid/30% acetonitrile.

Mass-Spectrometric Analysis

An ion trap mass spectrometer (LCQdeka, ThermoFinnigan, San Jose) which was connected directly to a high pressure liquid chromatography appliance (LC-MS) was used for analyzing the peptides. A reversed-phase column ($C_{18}$ phase) was used as the separation column. The peptides were dissolved in eluent A (0.025% (v/v) trifluoroacetic acid) and injected. They were eluted with a gradient of eluent B (0.025% (v/v) trifluoroacetic acid/84% (v/v) acetonitrile). The eluting peptides were recognized automatically by the acquisition software in the instrument and fragmented for identification. In this way, it was possible to determine the identities of the peptides unambiguously.

The following results were expected on the basis of the experimental mixture:
- all the peptides from the SDS-7 mixture were to be detected in the form of four identically intensive signals which did not show any isotope effect in the chromatography.
- peptides from interleukin-4 were to appear in the form of a doublet of signals having a mass difference of 17 Da.

Figure 2:
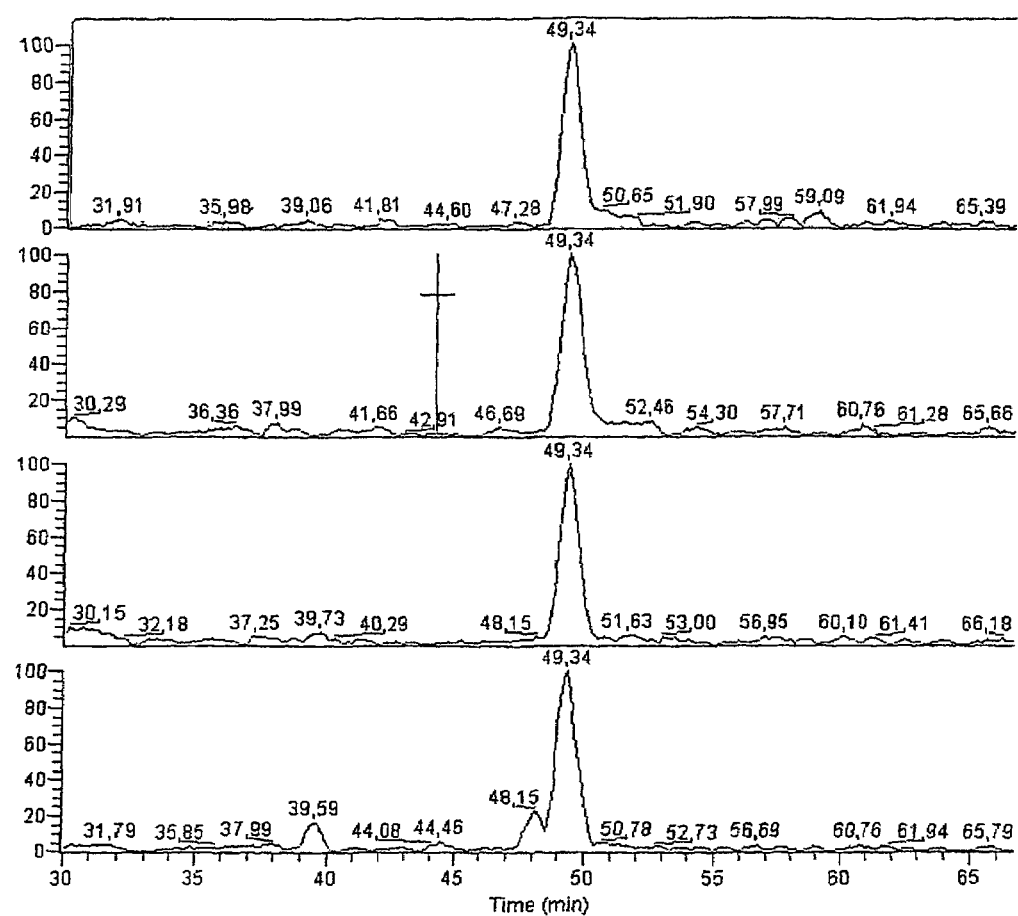
Figure 3:
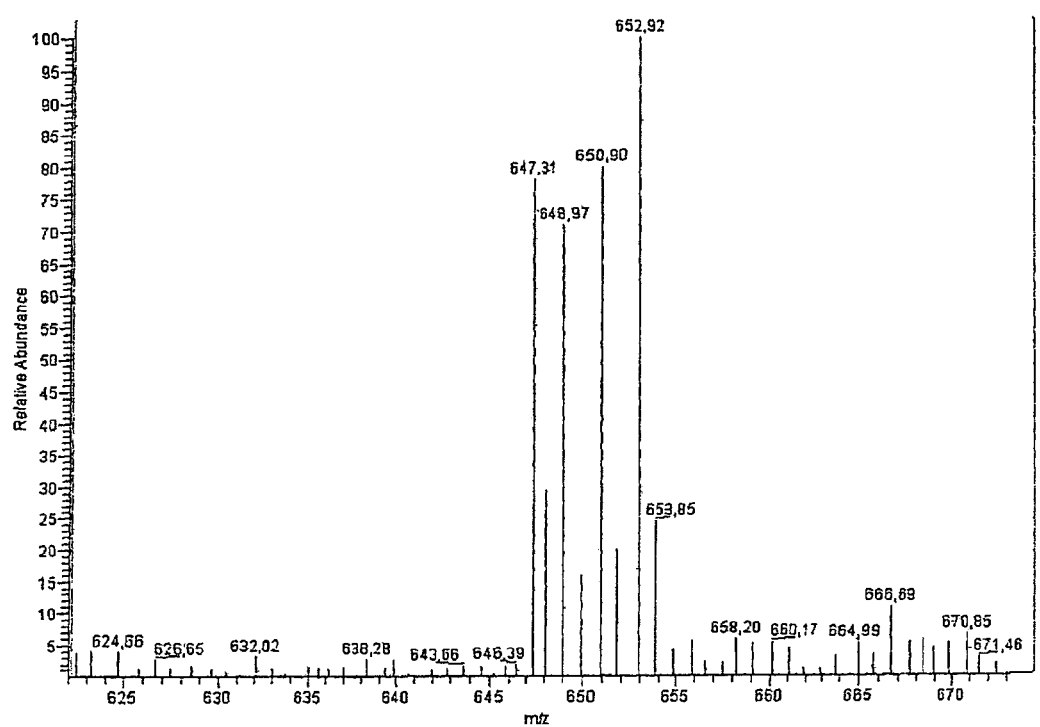

FIG. 2 shows the ion traces for the four differently labeled variants of the peptide LQGIVSWGSGCAQK from Trypsinogen. From the top to the bottom, the traces relate to the peptide which has been labeled by the affinity tags with 0, 5, 11 and 17 isotope labels. It is not possible to measure any retention difference between variants. FIG. 3 shows the appurtenant MS spectrum, which contains a quadruplet of almost equally intense signals. The identity of the peptide was confirmed by means of MS/MS experiments.

Figure 4:
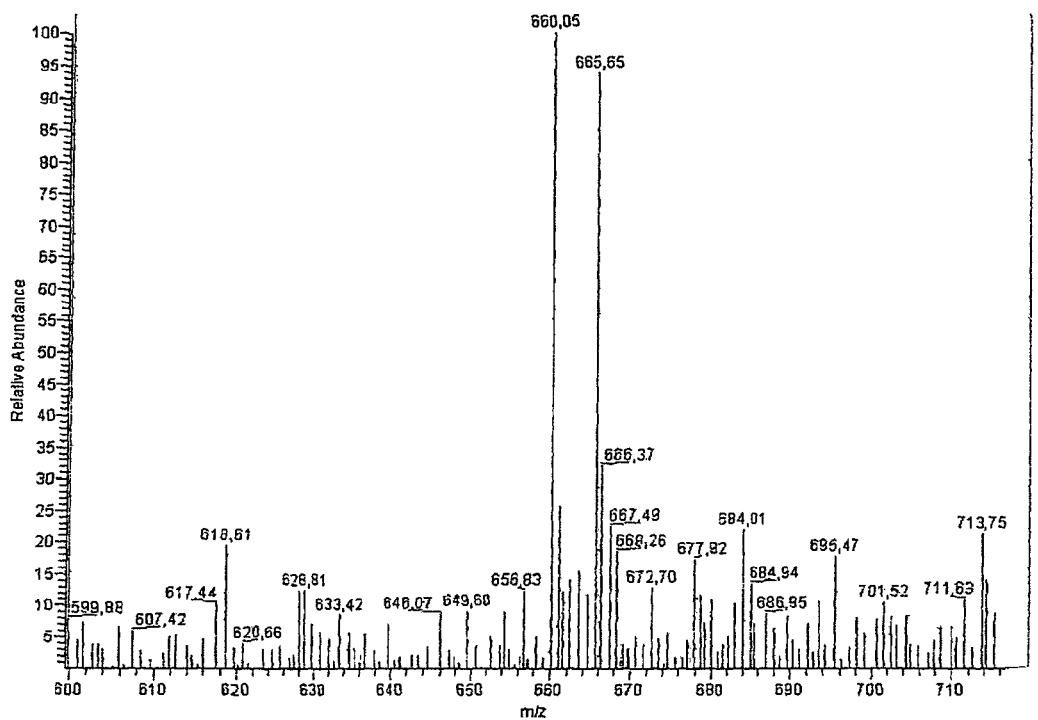

FIG. 4 shows the signals of the peptide NLWGLAGLN-SCPVK from interleukin-4. As expected, a doublet of signals is seen, with the intensity ratio being 1:1. In this way, the signal can be distinguished clearly from peptides which are unlabeled and which were purified by nonspecific adsorption on the affinity column. The identity of the peptide was confirmed by means of MS/MS experiments.

FIG. 2: The ion traces for the m/z values 647.3 Da, 648.9 Da, 650.9 Da and 652.9 Da. The traces relate to the triply charged ion of the peptide LQGIVSWGSGCAQK in the forms in which it is reacted with Examples 38 to 41. The identity of the peptides was confirmed by means of MS/MS experiments.

FIG. 3: MS spectrum of the LC peaks shown in FIG. 2. The peptide ion is triply charged.

FIG. 4: MS spectrum of the triply charged ion of the peptide NLWGLAGLNSCPVK from interleukin-4. Since it was only present in sample 1, a doublet of signals appears, with this doublet corresponding to the peptide possessing 0 and, respectively, 17 isotope labels.

The invention claimed is:

1. An organic compound of the formula (II),

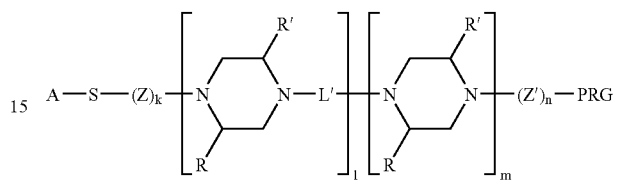

(II)

in which the groups A, PRG, S, Z, L', Z' and k, l, m and n, are defined as follows:

A is the acyl residue of an affinity ligand selected from biotinyl and a biotin derivative, or
is a functional group which is bound to a polymeric support, and is a support-bound hydroxyl, carboxyl or amino group, PRG is the residue of a protein-reactive group, selected from

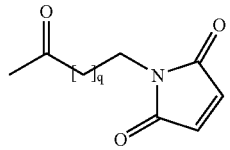

in which q = 0–4,

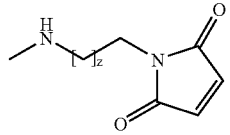

in which z = 0–5,

—CO—(CH$_2$)$_r$—Cl in which r=1–10, and
—CO—CH=CH$_2$;

S is an acid-cleavable group of the formula

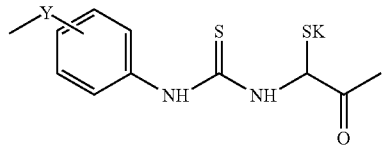

in which Y is a spacer selected from NH, NH—CH$_2$, NH—CH$_2$—CH$_2$—NH—CO and CH$_2$—CO, where Y can be in the ortho, meta or para position in relation to NH,
and in which SK is the side chain residue of an α-amino acid of the formula SK—CH(NH$_2$)—COOH selected form the side chains of the 20 natural amino acids, which, in the case of SKs other than an H atom, can be present in the D, L or racemic from, Z is the residue of an amino acid, which is not labeled or which can contain $^{13}$C or $^{15}$N labels, or a combination of these labels, selected from the 20 natural proteinogenic amino acids, and residues of ω-amino acids, selected from NH—(CH$_2$)$_2$—CO and CO—(CH$_2$)$_2$—NH, which, where appropriate, can be in the D, L or racemic form, L' is a bridge which makes possible, or facilitates, the covalent linkage of two piperazine residues, which can, where appropriate, contain $^{13}C$ or $^{15}N$ isotope labels or a combination of these labels, selected from CO—CO, CO—(CH$_2$)$_s$—CO and also CO-arylene-CO, CO—CH$_2$—NH—CO—NH—CH$_2$—CO, CO—NH—CH$_2$—CO, CO—CH$_2$—NH—CO, CO—CH$_2$—NH—CO—CO—NH—CH$_2$—CO, CO—CH$_2$—NH—CO—(CH$_2$)$_s$—CO—NH—CH$_2$—CO, CO—CH$_2$—NH—CO-arylene-CO—NH—CH$_2$—CO, (CH$_2$)$_s$—NH—CO—CO—NH—(CH$_2$)$_s$, (CH$_2$)$_3$—NH—CO—CO—NH—(CH$_2$)$_3$, (CH$_2$)$_s$—CO, (CH$_2$)$_2$—CO, CO and CS, where s is an integer between 1 and 6, R and R' are hydrogen, Z' is the residue of an amino acid, which differs from Z in the different orientation in regard to the terminal CO and NH groups; it may not be labeled or may contain $^{13}C$ or $^{15}N$ labels, or a combination of these labels selected from the 20 natural proteinogenic amino acids, and residues of ω-amino acids, selected from NH—(CH$_2$)$_2$—CO and CO—(CH$_2$)$_2$—NH, which, where appropriate, can be in the D, L or racemic form, k, l, m and n can, independently of each other, in each case be numbers between 0 and 10, where the sum of k+l+m+n is greater than 0 and less than 20, with the proviso that at least one of Z, L', and Z' is labeled with $^{13}C$ and/or $^{15}N$;

or a pharmaceutically acceptable salt thereof.

2. A compound as claimed in claim 1, characterized in that Z is the residue of glycine.

3. A compound as claimed in claim 1 or 2, characterized in that Z' is the residue of glycine.

4. A compound as claimed in claim 1, characterized in that A is an amino-functionalized resin based on polyethylene glycol or silica gel.

5. A process for preparing a compound as claimed in claim 1, in which i) a protected intermediate of the formula (III)

$$SG-(Z)_k-\left[N\underset{\phantom{x}}{\diagup\diagdown}N-L'\right]_l\left[N\underset{\phantom{x}}{\diagup\diagdown}N\right]_m-(Z')_n-SG' \quad (III)$$

in which SG and SG' are two orthogonal protecting groups, selected from benzyloxycarbonyl, Boc, and Fmoc, is prepared, ii) the protecting group SG is first of all detached from the intermediate of the formula (III) and, after that, another amino acid derivative, which carries a protecting group SG, which is identical to, or different from, the detached protecting group, on the α-amino function, is attached, with a derivative of the formula (IV), $$SG-NH-CH(SK)-CO-(Z)_k-\left[N\underset{\phantom{x}}{\diagup\diagdown}N-L'\right]_l\left[N\underset{\phantom{x}}{\diagup\diagdown}N\right]_m-(Z')_n-SG' \quad (IV)$$

in which SK is the side chain of an amino acid, as defined in claim 1, being obtained, iii) after the protecting group SG' has been detached from the derivative of the formula (IV), the latter is reacted with the derivative or the activated precursor of the derivative of the formula (V)

$$U-PRG \quad (V)$$

in which U is a group which enables PRG to be linked to Z' or, where appropriate, to another end group of L, iv) the terminal protecting group SG is detached, with a conjugate of the formula (VI)

$$H_2N-CH(SK)-CO-(Z)_k-\left[N\underset{\phantom{x}}{\diagup\diagdown}N-L'\right]_l\left[N\underset{\phantom{x}}{\diagup\diagdown}N\right]_m-(Z')_n-PRG \quad (VI)$$

being obtained, v) an affinity ligand A-OH or A-NH$_2$, or a hydroxyl-functionalized, carboxyl-functionalized or amino-functionalized solid phase A-OH or A-NH$_2$, or an activated form thereof, is reacted with a compound of the formula (VII)

$$H-Y-\text{C}_6\text{H}_4-NH_2 \quad (VII)$$

in which Y is as defined in claim 1, which can optionally carry a protecting group selected from the group benzyloxycarbonyl, Boc, and Fmoc, to give the derivative of the formula (VIII)

$$A-Y-\text{C}_6\text{H}_4-NH_2 \quad (VIII)$$

vi) the derivative of the formula (VIII) is then converted, after prior elimination of an optionally introduced protecting group, into a corresponding isothiocyanate, vii) the isothiocyanate is then coupled to the conjugate of the formula (VI) to give the thiourea of the formula (IX), and

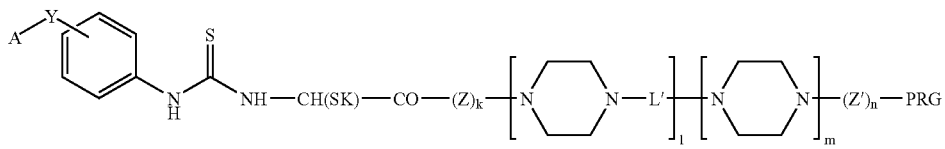

(IX)

viii) in an optional last step, protecting groups which are still present are eliminated, with it being possible to carry out the consecutive steps v) and vi) at any arbitrary time prior to step vii).

6. A process for preparing a compound as claimed in claim 1, in which i) a protected intermediate of the formula (III)

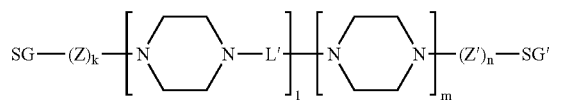

(III)

in which SG and SG' are two orthogonal protecting groups selected from benzyloxycarbonyl, Boc, and Fmoc, is prepared, ii) the protecting group SG is first of all detached from the intermediate of the formula (III) and, after that, another amino acid derivative, which carries a protecting group SG, which is identical to, or different from, the detached protecting group, on the α-amino function, is attached, with a derivative of the formula (IV),

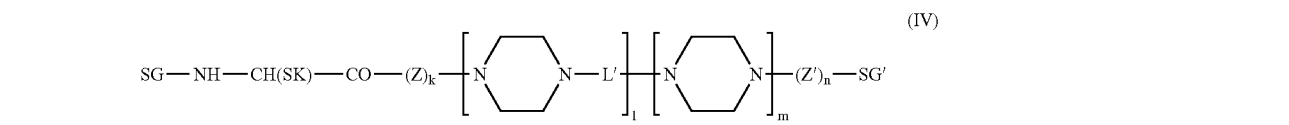

(IV)

in which SK is the side chain of an amino acid, as defined in claim 1, being obtained, iii) the terminal protecting group SG is detached, with a conjugate of the formula (VI')

iv) an affinity ligand A-OH or A-NH$_2$, or a hydroxyl-functionalized, carboxyl-functionalized or amino-functionalized solid phase A-OH or A-NH$_2$, or an activated form thereof, is reacted with a compound of the formula (VII)

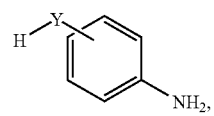

(VII)

in which Y is defined as in claim 1, which can optionally carry a protecting group, to give the derivative of the formula (VIII)

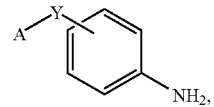

(VIII)

v) the derivative of the formula (VIII) is then converted, after the prior elimination of an optionally introduced protecting group, into a corresponding isothiocyanate, vi) the isothiocyanate is then coupled to the conjugate of the formula (VI') to give the thiourea of the formula (X'),

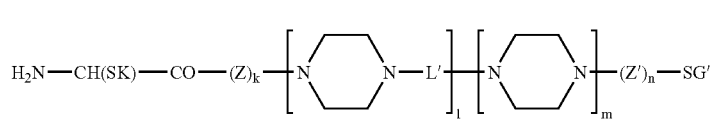

(VI')

being obtained,

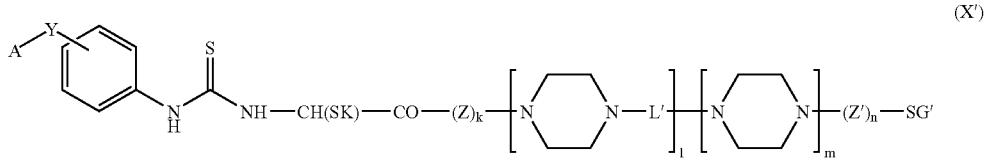

and vii) after the protecting group SG' has been detached from the thiourea of the formula (X'), the latter is reacted with the derivative of a protein-reactive group or the activated precursor of the derivative of the formula (V)

U-PRG     (V)

in which U is a group which enables PRG to be linked to Z' or, where appropriate, to another end group of L, and viii) in an optional last step, protecting groups which may still be present are eliminated, with it being possible to carry out the consecutive steps iv) and v) at any arbitrary time prior to step vi).

7. A method for the mass spectrometric analysis of proteins, comprising: a tagging proteins in at least one mixture of proteins with at least one isotope-labeled compound according to claim 1, b) if necessary, cleaving the tagged proteins to produce tagged peptides, c) purifying the tagged peptides by affinity chromatography, and d) analyzing the tagged peptides by mass spectrometry.

8. The method of claim 7 wherein one or more of said proteins is identified.

9. The method of claim 7 wherein the relative level of expression of one or more proteins in one or more protein-containing samples is determined.

10. A kit for the mass-spectrometric analysis of proteins, comprising, as reagents, one or more differently isotope-labeled compounds as claimed in claim 1.

* * * * *